United States Patent
Sanders et al.

(10) Patent No.: US 10,966,950 B2
(45) Date of Patent: Apr. 6, 2021

(54) USE OF AN RXR AGONIST IN TREATING HER2+ CANCERS

(71) Applicants: Io Therapeutics, Inc., Houston, TX (US); Board of Regents, The University of Texas System, Austin, TX (US)

(72) Inventors: Martin E. Sanders, Seattle, WA (US); Powel H. Brown, Houston, TX (US)

(73) Assignees: Io Therapeutics, Inc., Houston, TX (US); Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 16/898,230

(22) Filed: Jun. 10, 2020

(65) Prior Publication Data

US 2020/0390736 A1    Dec. 17, 2020

Related U.S. Application Data

(60) Provisional application No. 62/860,133, filed on Jun. 11, 2019.

(51) Int. Cl.
| | | |
|---|---|---|
| A61K 31/185 | (2006.01) | |
| A61K 39/395 | (2006.01) | |
| A61K 31/216 | (2006.01) | |
| A61P 35/00 | (2006.01) | |
| A61K 31/4709 | (2006.01) | |
| A61K 38/24 | (2006.01) | |
| A61K 31/517 | (2006.01) | |

(52) U.S. Cl.
CPC ........ *A61K 31/216* (2013.01); *A61K 31/4709* (2013.01); *A61K 31/517* (2013.01); *A61K 38/24* (2013.01); *A61K 39/3955* (2013.01); *A61P 35/00* (2018.01); *A61K 31/185* (2013.01)

(58) Field of Classification Search
CPC . A61K 31/185; A61K 39/395; A61K 2300/00
See application file for complete search history.

(56) References Cited

U.S. PATENT DOCUMENTS

| | | | |
|---|---|---|---|
| 4,756,911 A | 7/1988 | Drost | |
| 5,378,475 A | 1/1995 | Smith | |
| 5,455,265 A | 10/1995 | Chandraratna | |
| 5,466,861 A | 11/1995 | Dawson et al. | |
| 5,663,367 A | 9/1997 | Vuligonda et al. | |
| 5,675,033 A | 10/1997 | Vuligonda et al. | |
| 5,728,846 A | 3/1998 | Vuligonda et al. | |
| 5,739,338 A | 4/1998 | Beard et al. | |
| 5,763,635 A | 6/1998 | Vuligonda et al. | |
| 5,773,594 A | 6/1998 | Johnson et al. | |
| 5,776,699 A | 7/1998 | Klein et al. | |
| 5,780,647 A | 7/1998 | Vuligonda et al. | |
| 5,817,836 A | 10/1998 | Vuligonda et al. | |
| 5,856,490 A | 1/1999 | Teng | |
| 5,877,207 A | 3/1999 | Klein et al. | |
| 5,917,082 A | 6/1999 | Vuligonda et al. | |
| 5,919,970 A | 7/1999 | Song et al. | |
| 5,952,345 A | 9/1999 | Klein et al. | |
| 5,958,954 A | 9/1999 | Klein et al. | |
| 5,965,606 A | 10/1999 | Teng | |
| 5,998,655 A | 12/1999 | Vuligonda et al. | |
| 6,008,204 A | 12/1999 | Klein et al. | |
| 6,048,873 A | 1/2000 | Vasudevan et al. | |
| 6,034,242 A | 3/2000 | Vuligonda et al. | |
| 6,037,488 A | 3/2000 | Song et al. | |
| 6,043,381 A | 3/2000 | Vuligonda et al. | |
| 6,063,768 A | 5/2000 | First | |
| 6,087,505 A | 7/2000 | Vuligonda et al. | |
| 6,090,810 A | 7/2000 | Klein et al. | |
| 6,114,533 A | 9/2000 | Vuligonda et al. | |
| 6,117,987 A | 9/2000 | Johnson et al. | |
| 6,147,224 A | 11/2000 | Vuligonda et al. | |
| 6,187,750 B1 | 2/2001 | Chein | |
| 6,211,385 B1 | 4/2001 | Vuligonda et al. | |
| 6,218,128 B1 | 4/2001 | Klein et al. | |
| 6,225,494 B1 | 5/2001 | Song et al. | |
| 6,228,848 B1 | 5/2001 | Klein et al. | |
| 6,235,923 B1 | 5/2001 | Song et al. | |
| 6,313,163 B1 | 11/2001 | Vuligonda et al. | |
| 6,313,168 B1 | 11/2001 | Pacifici et al. | |
| 6,387,950 B2 | 5/2002 | Nehme | |

(Continued)

FOREIGN PATENT DOCUMENTS

| | | |
|---|---|---|
| EP | 2556827 A1 | 2/2013 |
| JP | 2010-280585 A | 12/2010 |

(Continued)

OTHER PUBLICATIONS

Brown, Powel, MD, PhD. Retinoid receptors: Developing rexinoids for the prevention and treatment of breast cancer. 4nd International FASEB Conference on Retinoids. Clinical Cancer Prevention MD Anderson Cancer Center, Houston, Texas, USA, Jun. 12, 2018.
Corrigan et al., Ado-trastuzumab emtansine: a HER2-positive targeted antibody-drug conjugate. Ann Pharmacother, 48(11):1484-93 (2014) (abstract).
Dosing and Administration Guide for nerlynx® (neratinib) tablets, for oral use. Full Prescribing Information for nerlynx, Initial US. Approval 2017, Revised Jun. 2018 (41 pages).
Eisenhauer et al., New response evaluation criteria in solid tumours: Revised RECIST guideline (version 1.1). European Journal of Cancer, 45:228-247 (2009).
Full Prescribing Information for Gilotrif® (afatinib) tablets, for oral use, Initial U.S. Approval 2013, Revised Jan. 2018.

(Continued)

*Primary Examiner* — Samira J Jean-Louis
(74) *Attorney, Agent, or Firm* — K&L Gates LLP; Louis C. Cullman; David Diamond

(57) ABSTRACT

The present specification provides combinations of active agents for the improved treatment of Her2+ cancers and associated methods of treatments. The combinations comprise and RXR agonist and a Her2-targeted therapeutic agent and may optionally further comprise thyroid hormone.

17 Claims, 10 Drawing Sheets

(56) References Cited

U.S. PATENT DOCUMENTS

| | | |
|---|---|---|
| 6,403,638 B1 | 6/2002 | Vuligonda et al. |
| 6,521,624 B1 | 2/2003 | Klein et al. |
| 6,521,641 B1 | 2/2003 | Klein et al. |
| 6,538,149 B1 | 3/2003 | Vuligonda et al. |
| 6,555,690 B2 | 4/2003 | Johnson et al. |
| 6,610,744 B2 | 8/2003 | Teng et al. |
| 6,630,463 B2 | 10/2003 | Kikuchi et al. |
| 6,653,483 B1 | 11/2003 | Johnson et al. |
| 6,720,423 B2 | 4/2004 | Vasudevan et al. |
| 6,720,425 B2 | 4/2004 | Johnson et al. |
| 6,776,984 B1 | 8/2004 | Schwartz |
| 6,818,775 B2 | 11/2004 | Johnson et al. |
| 6,942,980 B1 | 9/2005 | Klein et al. |
| 7,048,946 B1 | 5/2006 | Wong |
| 7,105,566 B2 | 9/2006 | Chandraratna et al. |
| 7,166,726 B2 | 1/2007 | Vuligonda et al. |
| 8,101,662 B2 | 1/2012 | Chandraratna |
| 9,308,186 B2 | 4/2016 | Chandraratna |
| 9,655,872 B2 | 5/2017 | Chandraratna |
| 9,717,702 B2 | 8/2017 | Chandraratna |
| 10,039,731 B2 | 8/2018 | Chandraratna |
| 10,188,618 B2 | 1/2019 | Chandraratna |
| 2001/0037025 A1 | 11/2001 | Murray et al. |
| 2002/0156054 A1 | 10/2002 | Klein et al. |
| 2002/0173631 A1 | 11/2002 | Johnson et al. |
| 2002/0193403 A1 | 12/2002 | Yuan et al. |
| 2003/0013766 A1 | 1/2003 | Lamph et al. |
| 2003/0077664 A1 | 4/2003 | Zhao et al. |
| 2003/0144330 A1 | 7/2003 | Spiegelman |
| 2003/0219832 A1 | 11/2003 | Klein et al. |
| 2004/0049072 A1 | 3/2004 | Ardecky |
| 2004/0147611 A1 | 7/2004 | Yuan et al. |
| 2004/0037025 A1 | 11/2004 | Murray et al. |
| 2005/0004213 A1 | 1/2005 | Sinha et al. |
| 2005/0171151 A1 | 8/2005 | Yuan et al. |
| 2005/0181017 A1 | 8/2005 | Hughes |
| 2005/0244464 A1 | 11/2005 | Hughes |
| 2006/0286127 A1 | 12/2006 | Van Schaack et al. |
| 2007/0054882 A1 | 3/2007 | Klein et al. |
| 2007/0077652 A1 | 4/2007 | Peled et al. |
| 2007/0078129 A1 | 4/2007 | Lagu et al. |
| 2007/0122476 A1 | 5/2007 | Hanshew |
| 2007/0185055 A1 | 8/2007 | Jiang |
| 2007/0265449 A1 | 11/2007 | Vuligonda et al. |
| 2008/0102069 A1 | 5/2008 | Friess et al. |
| 2009/0004291 A1 | 1/2009 | Song |
| 2009/0136470 A1 | 5/2009 | Hilde et al. |
| 2009/0203720 A1 | 8/2009 | Zhao et al. |
| 2009/0227674 A1 | 9/2009 | Richon et al. |
| 2010/0298434 A1 | 11/2010 | Rouillard |
| 2011/0008437 A1 | 1/2011 | Altman |
| 2012/0115912 A1 | 5/2012 | Landreth |
| 2012/0238623 A1 | 9/2012 | Chandraratna |
| 2012/0309833 A1 | 12/2012 | Wagner et al. |
| 2013/0190395 A1 | 7/2013 | Chandraratna et al. |
| 2014/0235676 A1 | 8/2014 | Landreth |
| 2014/0286973 A1 | 9/2014 | Powell, Jr. |
| 2015/0038585 A1 | 2/2015 | Chandraratna et al. |
| 2015/0196517 A1 | 7/2015 | Chandraratna et al. |
| 2015/0342917 A1 | 12/2015 | Chandraratna et al. |
| 2016/0263189 A1 | 9/2016 | Burstein |
| 2017/0056348 A1 | 3/2017 | Chandraratna et al. |
| 2017/0119713 A1 | 5/2017 | Chandraratna et al. |
| 2017/0119714 A1 | 5/2017 | Chandraratna et al. |
| 2017/0136026 A1 | 5/2017 | Sliwkowski et al. |
| 2018/0064670 A1 | 3/2018 | Chandraratna et al. |
| 2018/0116985 A1 | 5/2018 | Chandraratna et al. |
| 2018/0263939 A1 | 9/2018 | Chandraratna et al. |
| 2018/0318241 A1 | 11/2018 | Chandraratna et al. |
| 2018/0369181 A1 | 12/2018 | Chandraratna et al. |
| 2019/0083441 A1 | 3/2019 | Chandraratna et al. |
| 2019/0117603 A1 | 4/2019 | Chandraratna et al. |
| 2019/0125705 A1 | 5/2019 | Chandraratna et al. |
| 2019/0201358 A1 | 7/2019 | Chandraratna et al. |
| 2019/0231726 A1 | 8/2019 | Chandraratna et al. |
| 2019/0298678 A1 | 10/2019 | Chandraratna et al. |
| 2019/0365681 A1 | 12/2019 | Chandraratna et al. |
| 2019/0381022 A1 | 12/2019 | Chandraratna et al. |
| 2020/0155488 A1 | 5/2020 | Chandraratna et al. |
| 2020/0155489 A1 | 5/2020 | Chandraratna et al. |
| 2020/0170985 A1 | 6/2020 | Chandraratna et al. |

FOREIGN PATENT DOCUMENTS

| | | |
|---|---|---|
| WO | 1994/012880 A2 | 6/1994 |
| WO | 1994/014777 | 7/1994 |
| WO | 1996/039374 A1 | 12/1996 |
| WO | 1997/009297 A2 | 3/1997 |
| WO | 1999/008992 A1 | 2/1999 |
| WO | 1999/033821 A1 | 7/1999 |
| WO | 1999/063980 A1 | 12/1999 |
| WO | 2000/020370 A1 | 4/2000 |
| WO | 2001/007028 A2 | 2/2001 |
| WO | 2002/089781 A2 | 11/2002 |
| WO | 2002/089842 | 11/2002 |
| WO | 2003/027090 A2 | 4/2003 |
| WO | 2003/062369 | 7/2003 |
| WO | 2003/078567 | 9/2003 |
| WO | 2003/093257 A1 | 11/2003 |
| WO | 2003/101928 | 12/2003 |
| WO | 2004/046096 | 6/2004 |
| WO | 2005/013949 A2 | 2/2005 |
| WO | 2007/041076 A2 | 4/2007 |
| WO | 2007/041398 | 4/2007 |
| WO | 2008/157394 A2 | 12/2008 |
| WO | 2010/132671 A1 | 11/2010 |
| WO | 2011/006157 A2 | 1/2011 |
| WO | 2013/020966 | 2/2013 |
| WO | 2013/090616 A1 | 6/2013 |
| WO | 2015/059632 A1 | 4/2015 |
| WO | 2016/144976 A1 | 9/2016 |
| WO | 2017/075610 | 5/2017 |
| WO | 2017/075612 A1 | 5/2017 |
| WO | 2017/155577 A1 | 9/2017 |
| WO | 2017/155578 A1 | 9/2017 |
| WO | 2019/046591 A1 | 3/2019 |
| WO | 2019/060600 A1 | 3/2019 |

OTHER PUBLICATIONS

Full Prescribing Information for Herceptin® (trastuzumab) for injection, for intravenous use, Initial U.S. Approval 1998, Revised Nov. 2018.

Full Prescribing Information for Perjeta® (pertuzumab) for injection, for intravenous use, Initial U.S. Approval 2012, Revised Dec. 2018.

Highlights of Prescribing Information for Tukysa® (tucatinib) tablets, for oral use, Initial U.S. Approval 2020, Revised Apr. 2020.

Highlights of Prescribing Information for Tykerb® (lapatinib) tablets, for oral use, Initial U.S. Approval 2007, Revised Dec. 2018 (Full prescribing information also enclosed).

International Search Report and Written Opinion dated Aug. 1, 2019 for International Application No. PCT/US2019/036594 filed on Jun. 11, 2019.

Rinnerthaler et al., Review: HER2 directed antibody-drug-conjugates beyond T-DM1 in breast cancer. International Journal of Molecular Sciences, 20, 1115, 17 pp. (2019).

Seymour et al., iRECIST: Guidelines for response criteria for use in trials testing immunotherapeutics. Manuscript. Presented in part at the EORTC-NCI-AACR 2016 Meeting (Munich, Nov. 29-Dec. 2, 2016).

Inoue et al., Rexinoids isolated from Sophora tonkinensis with a gene expression profile distinct from the synthetic rexinoid bexarotene. J. Nat. Prod. 77:1670-1677 (2014).

"Intranasal medication delivery—brief overview of the concept." Intranasal.net. Accessed Feb. 24, 2017.

Io Therapeutics, Inc. Brochure for the Symposium on IRX4204 at the 11th International Conference on Alzheimer's and Parkinson's Diseases (2013).

Jassem et al., A randomized phase III trial comparing bexarotene/cisplatin/vinorelbine versus cisplatin/vinorelbine in chemotherapy-

(56) References Cited

OTHER PUBLICATIONS naïve-patients with advanced or metastatic non-small cell lung cancer (NSCLC). Journal of Clinical Oncology, 2005 ASCO Annual Meeting Proceedings, vol. 23, No. 16S, Part I of II (Jun. 1 Supllement), Abstract 7024 (2005).
Johnson et al., Synthesis and biological activity of high-affinity retinoic acid receptor antagonists. Bioorganic & Medicinal Chemistry, vol. 7, No. 7, pp. 1321-1338 (1999).
Kagechika et al., Synthetic retinoids: recent developments concerning structure and clinical utility. Journal of Medicinal Chemistry, vol. 48, No. 19: 5875-5883, (2005).
Kawata et al., RXR partial agonist produced by side chain repositioning of alkoxy RXR full agonist retains antitype 2 diabetes activity without the adverse effects. J. Med. Chem. 58(2):912-926 (2015).
Kimura et al., IL-6: Regulator of Treg/Th17 balance. Eur. J. Immunol., 40:1830-1835 (2010).
Kim et al., Immunopathogenesis and therapy of cutaneous T cell lymphoma. Science in Medicine, The JCI Textbook of Molecular Medicine. Editors Marks et al., p. 164 (2007).
Klein et al., Cardiovascular involvement in general medial conditions. Thyroid disease and the heart. Circulation, 116:1725-1735 (2007).
Klein et al., Identification and functional separation of retinoic acid receptor neutral antagonists and inverse agonists. The Journal of Biological Chemistry, vol. 271, No. 37, pp. 22692-22696, 1996.
Knol et al., Absence of modulation of CD4+CD25high regulatory T cells in CTCL patients treated with bexarotene. Experimental Dermatology, 19:e95-e102 (2010).
Kotani et al., A naturally occurring rexinoid, honokiol, can serve as a regulator of various retinoid X receptor heterodimers. Biol. Pharm. Bull. 35(1):1-9 (2012).
Laclair et al., Treatment with bexarotene, a compound that increases apolipoprotein-E, provides no cognitive benefit in mutant APP/PS1 mice, Molecular Neurodegeneration 8:18 (10pp) (2013).
Lampen et al., Effects of receptor-selective retinoids on CYP26 gene expression and metabolism of all-trans-retinoic acid in intestinal cells. Drug Metabolism & Disposition, vol. 29, No. 3, pp. 742-747 (2001).
Lefebvre et al., Retinoid X receptors: common heterodimerization partners with distinct functions. Trends Endocrinol. Metab. 21:676-683 (2010).
Levasque et al., Nur77 and retinoid X receptors: crucial factors in dopamine-related neuroadaptation. Trends in Neuroscience, vol. 30, No. 1, pp. 22-30 (2007).
Li et al., Distinct Mechanisms of Glucose Lowering by Specific Agonists for Peroxisomal Proliferator Activated Receptor gamma and Retinoic Acid X Receptors, Journal of Biological Chemistry 280(46):38317-38327, 2005.
Liu et al., Combination Therapy of Insulin-Like Growth Factor Binding Protein-3 and Retinoid X Receptor Ligands Synergize on Prostate Cancer Cell Apoptosis In vitro and In vivo. Clin Cancer Res, 11(13):4851-4856 (2005).
Lowenthal et al., The Ethics of Early Evidence—Preparing for a Possible Breakthrough in Alzheimer's Disease, N Engl J Med., 367(6):488-490 (2012).
Macchia et al., RXR receptor agonist suppression of thryoid function: central effects in the absence of thyroid hormone receptor. Am. J. Physiol. Endocrinol. Metab., vol. 283, pp. E326-E331 (2002).
Mangelsdorf et al., Characterization of three RXR genes that mediate the action of 9-cis retinoic acid. Genes and Development 6:329-344 (1992).
Marketwire 2012: IRX4204 as a Potential Disease-Modifying Treatment for Alzheimer's Disease.
Marks et al., Science in Medicine: The JCI textbook of Molecular Medicine, p. 164 (2007).
Martin et al., Induction of the fatty acid transport protein 1 and acyl-CoA synthase genes by dimer-selective rexinoids suggests that the peroxisome proliferator-activated receptor-retinoid X receptor heterodimer is their molecular target. JBC 275(17):12612-12618 (2000).
McFarland et al., Low dose bexarotene treatment rescues dopamine neurons and restores behavioral function in models of Parkinson's disease. ACS Chem. Neurosci. 4:1430-1438 (2013).
Migliore, Intranasal Delivery of GDNF for the Treatment of Parkinson's Disease. Doctoral Thesis, Pharmaceutical Sciences, Northeastern University, Boston, MA (2008).
Miller et al., Initial clinical trial of a selective retinoid X receptor ligand, LGD1069. J Clin Oncol., 15(2):790-795 (1997).
Monahan et al., Neuroinflammation and peripheral immune infiltration in Parkinson's disease: an autoimmune hypothesis. Cell Transplant, 17:363-372 (2008).
Morris & Burns, Insulin: An Emerging Treatment for Alzheimer's Disease Dementia? Curr. Neurol. Neurosci. Rep. 12(5):520-527 (2012).
Munhoz et al., Parkinson's disease and thyroid dysfunction. Parkinsonism & Related Disorders, 10(6):381-383 (2004).
National Multiple Sclerosis Society, Medications, accessed May 12, 2017, pp. 1-5.
Natrajan et al., Retinoid X receptor activation reverses age-related deficiencies in myelin debris phagocytosis and remyelination. Brain A Journal of Neurology, 138:3581-3597 (2015).
Nishimaki-Mogami et al., The RXR agonists PA024 and HX630 have different abilities to activate LXR/RXR and to induce ABCA1 expression in macrophage cell lines. Biochemical Pharmacology, 76: 1006-1013 (2008).
Ohsawa et al., Modification of the lipophilic domain of RXR agonists differentially influences activation of RXR heterodimers. ACS Med Chem Lett., 1:521-525 (2010).
Olson et al., Immunomodulation as a neuroprotective and therapeutic strategy for Parkinson's disease. Curr Opin Pharmacol. 26:87-95 (2016).
Park et al., Salvage chemotherapy of gemcitabine, dexamethasone, and cisplatin (GDP) for patients with relapsed or refractory peripheral T-cell lymphomas: a consortium for improving survival of lymphoma (CISL) trial. Ann. Hematol., vol. 94, No. 11, pp. 1845-1851, see abstract (2015).
Perlmann et al., A novel pathway for vitamin a signaling mediated by RXR heterodimerization with NGFI-B and NURR1. Genes & Develop. 9:769-782 (1995).
Petty et al., Weekly paclitaxel (Taxol®), carboplatin (Paraplatin®), and bexarotene (Tagretin®) for the treatment of patients with advanced non-small cell lung cancer: Efficacy results from a Phase I/II study. Journal of Clinical ONcolocy, 2005 ASCO Annual Meeting Proceedings, vol. 23, No. 16S, Part I of II (Jun. 1 Supplement) Abstract 7243 (2005).
Pierrot et al., Targretin Improves Cognitive and Biological Markers in a Patient with Alzheimer's Disease. Journal of Alzheimer's Disease, 49:271-276 (2016).
Price et al., Comment on ApoE-directed Therapeutics Rapidly Clear beta-Amyloid and Reverse Deficits in AD Mouse Models. Science 340:924-d (2013).
Ramaswamy et al., Trophic factors therapy in Parkinson's disease. Prog. Brain Res., 175:201-216 (2009).
Ramlau et al., Randomized phase III trial comparing bexarotene (L1069-49)/cisplatin/vinorelbine with cisplatin/vinorelbine in chemotherapy-naïve patients with advanced or metastic non-small-cell lung cancer: Spirit I. J. Clin. Oncol., 26:1886-1892 (2008).
Reynolds et al., Regulatory T cells attenuate Th17 cell-mediated nigrostriatal dopaminergic neurodegneration in a model of Parkinson's disease. J. Immunol., vol. 184, pp. 2261-2271 (2010).
Riancho et al., Neuroprotective effect of bexarotene in SOD1G93A mouse model of amyotrophic lateral sclerosis. Frontiers Cellular Neuroscience 9:Article 250 (2015).
Rigas et al., Emerging role of rexinoids in non-small cell lung cancer: Focus on bexarotene. The Oncologist, 10:22-33 (2005).
Rizvi et al., A phase I study of LGD1069 in adults with advanced cancer. Clin. Cancer Res., 5:1658-1664 (1999).
Sacchetti et al., Requirements for heterodimerization between orphan nuclear receptor Nurr1 and Retinoid X Receptors. The Journal of Biological Chemistry, 277(38):35088-35096 (2002).

(56) References Cited

OTHER PUBLICATIONS

Salama et al., Role of L-thyroxin in counteracting rotenone induced neurotoxocity in rats. Environmental Toxicology and Pharmacology, 35:270-277 (2013).
Sherman et al., Central hypothyroidism associated with retinoid X receptor-selective ligands. The New England Journal of Medicine, vol. 340, No. 14, pp. 1075-1079 (1999).
Silvestroff et al., Cuprizone-induced demyelination in the rat cerebral cortex and thyroid hormone effects on cortical remyelination. Experimental Neurology, 235, pp. 357-367 (2012).
Smit et al., Bexarotene-induced hypothrodism: bexarotene stimulates the peripheral metabolism of thyroid hormones. J. Clin. Endocrinol. Metab., 92(7):2496-2499 (2007).
Sufi et al., Prevention and treatment of experimental breast cancer with the combination of a new selective estrogen receptor modulator, Arzoxifene, and a new rexinoid, LG 100268. Clin Cancer Res, 8:3270-3275 (2002).
Takahashi et al., Novel retinoid X receptor antagonists: specific inhibition of retinoid synergism in RXR-RAR heterodimer actions. Journal of Medicinal Chemistry, vol. 45, No. 16, pp. 3327-3330 (2002).
Teng et al., Identification of highly potent retinoic acid receptor alpha-selective antagonists. Journal of Medicinal Chemistry, vol. 40, pp. 2445-2451 (1997).
Tesseur et al., Comment on ApoE-directed Therapeutics Rapidly Clear beta-Amyloid and Reverse Deficits in AD Mouse Models. Science, 340:924-e (2013).
Tovar-Y-Romo et al., Trophic factors as modulators of motor neuron physiology and survival: implications for ALS therapy. Frontiers in Cellular Neuroscience, 8:Article 61 (2014).
Trillo et al., Ascending monoaminergic systems alterations in Alzheimer's disease. Translating basic science into clinical care. Neuroscience and Biobehavioral Riviews, 37:1363-1379 (2013).
Assaf et al., Minimizing adverse side-effects of oral bexarotene in cutaneous T-cell lymphoma: an expert opinion. British Journal of Dermatology, 155, pp. 261-266 (2006).
Diab et al., Ligands for the peroxisome proliferator-activated receptor-gamma and the retinoid X receptor exert additive anti-inflammatory effects on experimental autoimmune encephalomyelitis. Journal of Neuroimmunology, 148, pp. 116-126 (2004).
Extended European Search Report, dated Oct. 1, 2019, for European Application No. 16893789.4 filed Oct. 31, 2016.
Farmer et al., Retinoic acid receptor ligands based on the 6-cyclopropyl-2,4-hexadienoic acid. Bioorganic & Medicinal Chemistry Letters, 13:261-264 (2003).
Hsu et al., Generation and characterization of monoclonal antibodies directed against the surface antigens of cervical cancer cells. Hybrid Hybridomics, vol. 23, No. 2, pp. 121-125 (2004)—abstract.
Uslu et al., Doxazosin: a new cytotoxic agent for prostate cancer? BJU International, vol. 85, pp. 672-675 (2000).
Veeraraghavalu et al, Comment on ApoE-directed Therapeutics Rapidly Clear beta-Amyloid and Reverse Deficits in AD Mouse Models. Science 340:924-f, 2013.
Volakakis et al., Nurr1 and Retinoid X Receptor ligands stimulate Ret signaling in dopamine neurons and can alleviate alpha-synuclein disrupted gene expression. J. Neurosci., 35(42):14370-14385 (2015).
Walkley et al., Retinoic acid receptor anatagonism in vivo expands the numbers of precursor cells during granulopoiesis. Leukemia, vol. 16, No. 9, pp. 1763-1772 (2002).
Wallen-Mackenzie et al., Nurr1-RXR heterodimers mediate RXR ligand-induced signaling in neuronal cells. Genes and Development, 17: 3036-3047 (2003).
Wang et al., Selective brain penetrable Nurr1 transactivator for treating Parkinson's disease. Oncotarget 7 (7):7469-7479 (2016).
Wang, (2013) Slide presentation at the Symposium on IRX4204 at The 11th International Conference on Alzheimer's and Parkinson's Diseases: The Novel RXR agonist IRX4204 as a Potential Disease-Modifying Agent in Alzheimer's Disease.

WebMD, Common Drugs and Medicines to Treat Multiple Sclerosis; Drugs & Medications Search, accessed May 12, 2017; pp. 1-3.
Xiao et al., Retinoic acid increases Foxp3+ regulatory T cells and inhibits development of TH17 cells by enhancing TFG-β-driven Smad3 signaling and inhibiting IL-6 and IL-23 receptor expression. The Journal of Immunology, 181:2277-2284 (2008).
Xiao et al., Adenomatous polyposis coli (APC)-independent regulation of beta-catenin degradation via a retinoid X receptor-mediated pathway. Journal of Biological Chemistry, vol. 278, No. 32, pp. 29954-29962 (2003).
Yacila & Sari, Potential Therapeutic Drugs and Methods for the Treatment of Amyotrophic Lateral Sclerosis. Curr. Med. Chem., 21(31):3583-3593 (2014).
Yamada et al., Retinoid X receptor ligands: a patent review (2007-2013). Expert Opin. Ther. Patents, 24(4):443-452 (2014).
Zapata-Gonzalez et al., 9-cis-retinoic acid (9cRA), a retinoid X receptor (RXR) ligand, exerts immunosuppressive effects on dendritic cells by RXR-dependent activation: inhibition of peroxisome proliferator-activated receptor gamma blocks some of the 9cRA activities, and precludes them to mature phenotype development. The Journal of Immunogloy, 178:6130-6139 (2007).
Zhang et al., Thyroid hormone potentially benefits multiple sclerosis via facilitating remyelination. Mol. Neurobiol., 53, pp. 4406-4416 (2016).
Jones et al., Animal models of schizophrenia. British Journal of Pharmacology, 164:1162-1194 (2011).
Kabbinavar et al., An open-label phase II clinical trial of the RXR agonist IRX4204 in taxane-resistant, castration-resistant metastatic prostate cancer (CRPC). Journal of Clinical Oncology, vol. 32, No. 15 Suppl, p. 5073 (2014).
Kim, Chang H. Regulation of FoxP3+ regulatory T cells and Th17 cells by retinoids. Clinical and Developmental Immunology, vol. 2008, 12 pages (2008).
Koivusalo et al., The cytotoxicity of chemotherapy drugs varies in cervical cancer cells depending on the p53 status. Cancer Biology and Therapy, vol. 3278(11):1177-1183 (2004).
Liu et al., Mechanism of selective retinoid X receptor agonist-induced hypothroidism in the rat. Endocrinology, 143 (8):2880-2885 (2002).
Singaporean Written Opinion, dated Sep. 26, 2019, for Singaporean Application No. 11201807250P filed on Oct. 31, 2016.
Singaporean Written Opinion, dated Sep. 16, 2019, for Singaporean Application No. 11201807255Y filed on Oct. 31, 2016.
Supplementary European Search Report for European Patent Application Serial No. 16861057 dated May 22, 2019.
Supplementary European Search Report for European Patent Application Serial No. 16861059 dated May 16, 2019.
Vuligonda et al., Enantioselective syntheses of potent retinoid X receptor ligands: Differential biological activities of individual antipodes. J. Med. Chem., 44. pp. 2298-2303 (2001).
Alcala-Barraza et al., Intranasal delivery of neurotrophic factors BDNF, CNTF, EPO, and NT-4 to the CNS. Journal of Drug Targeting, 18(4179-190 (2009).
Altucci L et al., RAR and RXR modulation in cancer and metabolic disease. Nature Review Drug Discovery, vol. 6:793-810 (2007).
Alzforum 2013: Can Cancer Therapy Be Neurodegenerative Wonder Drug?
Annerbo et al., Review Article: A clinical review of the association of thyroid stimulating hormone and cognitive impairment. ISRN Endocrinology, vol. 2013, Article ID 856017, 6 pages (2013).
Balasubramanian et al., Suppression of human pancreatic cancer cell proliferation by AGN194204, an RXR-selective retinoid. Carcinogenesis, 2004, vol. 25, No. 8, pp. 1377-1385.
Balducci et al., The Continuing Failure of Bexarotene in Alzheimer's Disease Mice. J Alzheimers Dis., 46:471-482 (2015).
Benson et al., All-trans retinoic acid mediates enhanced T reg cell growth, differentiation, and gut homing in the face of high levels of co-stimulation. The Journal of Experimental Medicine, vol. 204, No. 8, pp. 1765-1774 (2007).
Beyer et al., Weight change and body composition in patients with Parkinson's disease. J. Am. DietAssoc., vol. 95, pp. 979-983 (1995).

(56) References Cited

OTHER PUBLICATIONS

Bilbao et al., Insulin-like growth factor-1 stimulates regulatory T cells and suppresses autoimmune disease. EMBO Mol. Med., 6(11):1423-1435 (2014).

Blumenschein et al., A randomized phase III trial comparing bexarotene/carboplatin/paclitaxel versus carboplatin/paclitaxel in chemotherapy-naive patients with advanced or metastatic non-small cell lung cancer (NSCLC). Journal of Clinical Oncology, 2005 ASCO Annual Meeting Proceedings, vol. 23, No. 16S, Part I of II, Abstract 7001 (2005).

Bordoni et al., Bexarotene improves TTP in untreated, advanced NSCLC, when given in combination with carboplalin/paclitaxel. Journal of Clinical Oncology, ASCO 2005 Annual Meeting, Abstract 7270.

Breen et al., Regulation of Thyroid-Stimulating Hormone beta-Subunit and Growth Hormone Messenger Ribonucleic Acid Levels in the Rat: Effect of Vitamin A Status, Endocrinology 136:543-9 (1995).

Cal et al., Doxazosin: a new cytotoxic agent for prostate cancer? BJU Int. 85:672-675 (2000).

Calza et al., Thyroid hormone activates oligodendrocyte precursors and increases a myelin-forming protein and NGF content in the spinal cord during experimental allergic encephalomyelitis. PNAS, vol. 99, No. 5, pp. 3258-3263 (2002).

Coya et al., Retinoic Acid Inhibits In Vivo Thyroid-Stimulating Hormone Secretion, Life Sciences, Pharmacology Letters, 60:247-50, 1997.

Cramer et al., ApoE-directed therapeutics rapidly clear β-amyloid and reverse deficits in AD mouse models. Science, 335(6075): 1503-1506 (2012).

Crowe et al., A retinoid X receptor (RXR)-selective retinoid reveals that RXR-alpha is potentially a therapeutic target in breast cancer cell lines, and that it potentiates antiproliferative and apoptotic responses to peroxisome proliferator-activated receptor ligands. Breast Cancer Res., vol. 6, No. 5, pp. R546-R555 (2004).

Cummings et al., Double-blind, placebo-controlled, proof-of-concept trial of bexarotene Xin moderate Alzheimer's disease. Alzheimer's Research & Therapy, 8:4 (2016).

Debnath & Berk, Th17 Pathway—Mediated Immunopathogenesis of Schizophrenia: Mechanisms and Implications. Schizophrenia Bulletin, 40(6):1412-1421 (2014).

Dell'Acqua ML et al., Functional and molecular evidence of myelin- and neuroprotection by thyroid hormone administration in experimental allergic encephalomyelitis. Neuropath. Appl. Neurobiol., 38:454-470 (2012).

D'Intino G et al., Triiodothyronine administration ameliorates the demyelination/remyelination ratio in a non-human primate model of multiple sclerosis by corrected tissue hypothyroidism. J Neuroendocrin., 23:778-790 (2011).

Dore et al., Insulin-like growth factor I protects and rescues hippocampal neurons against beta-amyloid- and human amylin-induced toxicity. Proc. Natl. Acad. Sci. USA, 94:4772-4777 (1997).

Duvic et al., Phase 2 and 3 Clinical Trial of Oral Bexarotene (Targretin Capsules) for the Treatment of Refractory or Persistent Early-Stage Cutaneous T-Cell Lymphoma, Arch Dermatol. 137:581-593, 2001.

Estephan et al., Phase II trial of gemcitabine (G), carboplatin (C) and bexarotene (B) in patients (pts) with newly diagnosed, locally-advanced or metastatic non-small cell carcinoma of the lung. Journal of Clinical Oncology, 2005 ASCO Annual Meeting Proceedings, vol. 23, No. 16S, Part I of II (Jun. 1 Supplement, Abstract 7308 (2005).

Elias et al., Retinoic acid inhibits TH17 polarization and enhances FoxP3 expression through a Stat-3/Stat-5 independent signaling pathway. Blood, vol. 111, No. 3, pp. 1013-1020 (2008).

Fitz et al., Comment on ApoE-directed Therapeutics Rapidly Clear beta-Amyloid and Reverse Deficits in AD Mouse Models. Science 340:924-c (2013).

Franco et al., Thyroid hormones promote differentiation of oligodendrocyte progenitor cells and improve remyelination after cuprizone-induced demyelination. Experimental Neurology, 212, pp. 458-467, 2008 (2008).

Freiherr et al., Intranasal Insulin as a Treatment for Alzheimer's Disease: A Review of Basic Research and Clinical Evidence. CNS Drugs 27:505-514 (2013).

Friling et al., Activation of retinoid X receptor increases dopamine cell survival in models for Parkinson's disease. BMC Neuroscience, 10: 146 (2009).

Fu et al., Thyroid hormone prevents cognitive deficit in a mouse model of Alzheimer's disease. Neuropharmacology, 58:722-729 (2010).

Gibb et al., The substantia nigra and ventral tegmental area in Alzheimer's disease and Down's sydrome. J. Neurol. Neurosurg. and Psychiatry, 52:193-200 (1989).

Golub et al., Molecular classification of cancer: Class discovery and class prediction by gene expression monitoring. Science, vol. 286, Oct. 15, 1999, pp. 531-537.

Gonzalez et al., T-cell-mediated regulation of neuroinflammation involved in neurodegenerative diseases. J Neuroinflam 11:201-212 (2014).

Govindan et al., Phase II trial of bexarotene capsules in patients with non-small-cell lung cancer (NSCLC) who have failed at least 2 prior systemic therapies for Stage IIIB/IV disease. Journal of Clinical Oncology, 2005 ASCO Annual Meeting Proceedings, vol. 23, No. 16S, Part I of II, Abstract 7116 (2005).

Graber et al., Protective autoimmunity in the nervous system. Pharmacol. Therapeut., 121:147-159 (2009).

Haugen et al., The Thyrotrope-Restricted Isoform of the Retinoid-X Receptor-γ1 Mediates 9-cis-Retinoic Acid Suppression of Thyrotropin-beta Promoter Activity. Molecular Endocrinology 11:481-9, 1997.

Henkel et al., Regulatory T-lymphocytes mediate amyotrophic lateral sclerosis progression and survival. EMBO Mol. Med., 5:64-79 (2012).

Hu et al., Imbalance between IL-17A-Producing Cells and Regulatory T Cells during Ischemic Stroke. Mediators of Inflammation 2014: Article ID 813045, 2014.

Huang et al. Retinoid X receptor gamma signaling accelerates CNS remyelination, Nature Neuroscience, 14(1):45-53, 2011 (Epub Dec. 5, 2010).

International Search Report and Written Opinion dated Mar. 28, 2013 for International Application Serial No. PCT/US2012/069566 filed on Dec. 13, 2012.

International Search Report and Written Opinion dated Jan. 5, 2017 for International Application Serial No. PCT/US2016/059770 filed Oct. 31, 2016.

International Search Report for PCT/US2007/011730 dated May 2, 2008.

International Search Report and Written Opinion dated Sep. 25, 2007 for International Application No. PCT/US2006/038252 filed on Oct. 2, 2006.

International Search Report and Written Opinion dated Dec. 29, 2016 for International Application No. PCT/US2016/059775 filed on Oct. 31, 2016.

International Search Report and Written Opinion dated Jan. 10, 2017 for International Application No. PCT/US2016/059776 filed on Oct. 31, 2016.

International Search Report and Written Opinion dated Dec. 29, 2016 for International Application No. PCT/US2016/059779 filed on Oct. 31, 2016.

International Search Report and Written Opinion dated May 22, 2017 for International Application No. PCT/US2016/059772 filed on Oct. 31, 2016.

International Search Report and Written Opinion dated Jan. 18, 2019 for International Application No. PCT/US2018/052031 filed on Sep. 20, 2018.

International Search Report and Written Opinion dated Dec. 11, 2018 for International Application No. PCT/US2018/048876 filed on Aug. 30, 2018.

(56) References Cited

OTHER PUBLICATIONS

Alsudais et al., Retinoid X receptor-selective signaling in the regulation of Akt/protein kinase B isoform-specific expression. The Journal of Biological Chemistry, vol. 291, No. 6, pp. 3090-3099 (2015).

USE OF AN RXR AGONIST IN TREATING HER2+ CANCERS

CROSS-REFERENCE

This application claims the benefit of U.S. Provisional Application No. 62/860,133, filed Jun. 11, 2019, the entire contents of which are incorporated by reference herein.

STATEMENT REGARDING FEDERALLY-SPONSORED RESEARCH

This invention was made with government support under grant number HHSN261201500018I awarded by the National Institutes of Health. The government has certain rights in the invention.

BACKGROUND

Compounds which have retinoid-like biological activity are well known in the art and are described in numerous United States patents including, but not limited to, U.S. Pat. Nos. 5,466,861; 5,675,033 and 5,917,082, all of which are herein incorporated by reference. Preclinical studies with rexinoids suggest that selective activation of retinoid X receptors (RXR), which modulate functions associated with differentiation, inhibition of cell growth, apoptosis and metastasis, may be useful in treating a variety of diseases associated with the biochemical functions modulated by RXR.

For example, TARGRETIN® (bexarotene), which is a retinoid X receptor (RXR) agonist with retinoic acid receptor (RAR) agonist activity as well, was approved by the U.S. Food and Drug Administration for the treatment, both oral and topical, of cutaneous manifestations of cutaneous T cell lymphoma in patients who are refractory to at least one prior systemic therapy. Encouraging results were obtained with TARGRETIN® in several Phase II studies in NSCLC. However, the pivotal Phase III clinical study did not show increased survival. One possible explanation for the limited success of bexarotene is that its activation of RAR decreases its efficacy as an anticancer agent. Thus, more selective RXR agonists may hold greater promise.

Agents targeting human epidermal growth factor receptor 2 (Her2), both anti-Her2 antibodies and inhibitors of the tyrosine kinase activity of Her2, have had significant, but not universal success in treating Her2$^+$ cancers, particularly Her2$^+$ breast cancers.

Treatments for cancer are ever evolving, gaining in specificity and sophistication. Early non-surgical cancer treatments generally targeted rapidly dividing cells which were more sensitive to radiological and chemical assault. Over time, more specific and less generally toxic treatments have been developed. Some treatments appear to have broad applicability, for example immune checkpoint inhibitors or rexinoids. Others are targeted to cancers that express a particular antigen or other biomarker involved in the regulation of proliferation or differentiation; including many monoclonal antibodies and kinase inhibitors. Yet as the variety of cancer treatments has grown, it has become ever harder to determine which treatments might be productively combined and for what indications.

SUMMARY

Herein disclosed are improved methods of treatment of Her2$^+$ cancers comprising treating a patient having a Her2$^+$ tumor with a combination of a Her2-targeting therapeutic agent and a RXR agonist capable of inhibiting cancer growth. In some embodiments the treatment combination further comprises thyroid hormone.

In some embodiments, the RXR agonist is capable of activating RXR/Nurr1 heterodimeric receptors. In some embodiments the RXR agonist is a compound of Formula I as disclosed herein below, or a pharmaceutically-acceptable salt thereof. In some embodiments the RXR agonist is a compound of Formula II as disclosed herein below, or a pharmaceutically-acceptable salt thereof. In some embodiments, compounds of Formula I and Formula II, and their pharmaceutically-acceptable salts, are referred to as means for activating RXR/Nurr1 heterodimeric receptors or rexinoid means for inhibiting tumor growth.

In some embodiments, Her2-targeting therapeutic agent is an inhibitor of Her2 kinase activity or Her2-mediated signaling. In some embodiments Her2-targeting therapeutic agent is therapeutic anti-Her2 antibody. Therapeutic antibodies may mediate antibody-dependent cellular cytotoxicity (ADCC) instead of, or in addition to, inhibiting signaling (kinase activity). Trastuzumab and pertuzumab are examples of therapeutic anti-Her2 antibodies, as disclosed herein below. In some embodiments such antibodies are referred to as immunoglobulin means for inhibiting Her2$^+$ tumor cell proliferation, means for mediating ADCC of Her2$^+$ tumor cells, or immunoglobulin means for inhibiting Her2 signaling.

In some embodiments, a Her2-targeting therapeutic agent is an antibody-drug conjugate comprising an anti-Her2 antibody. In some embodiments, the anti-Her2 antibody has therapeutic activity alone, while in other embodiments it does not, merely serving to deliver a cytotoxic agent to Her2$^+$ cells. Ado-trastuzumab emtansine is an example of a Her2-targeting antibody-drug conjugate, as disclosed herein below. In some embodiments such antibody-drug conjugates are referred to as means for delivering a cytotoxic agent to Her2$^+$ cells.

In some embodiments, the inhibitor of Her2 kinase activity or Her2-mediated signaling is a small organic molecule (small drug) inhibitor of Her2 kinase activity. Lapatinib and neratinib are examples of Her2 kinase inhibitors as disclosed herein below. In some embodiments such small drug inhibitor of Her2 kinase activity are referred to as small molecule means for inhibiting Her2 kinase activity.

In some embodiments, the Her2$^+$ cancer is a Her2$^+$ breast cancer. In some embodiments the Her2$^+$ cancer is a Her2$^+$ ovarian cancer, stomach cancer, adenocarcinoma of the lung, uterine cancer (such as serous endometrial carcinoma), gastric cancer, or salivary duct carcinoma.

In some embodiments, the herein disclosed treatments are carried out concurrently with other pharmaceutical therapies or radiotherapies. In alternative embodiments, the herein disclosed treatments are the exclusive therapy in the time interval in which they are conducted. In some embodiments, the herein disclosed treatments serve as a debulking treatment in preparation for subsequent surgical removal of tumor. In some embodiments, the herein disclosed treatments are applied as adjuvant therapy subsequent to surgical removal of tumor to address any residual disease or potential recurrent disease.

Other embodiments include combination drug compositions or formulations comprising at least one Her2-targeting therapeutic agent and at least one RXR agonist capable of inhibiting cancer growth. In other embodiments the combination (used for treatment) may include more than one agent in one or the other classification (Her2 targeting agent and/or RXR agonist). In still other embodiments the combination may further include thyroid hormone. In some embodiments the thyroid hormone is thyroxine.

DESCRIPTION

Figure 1A:
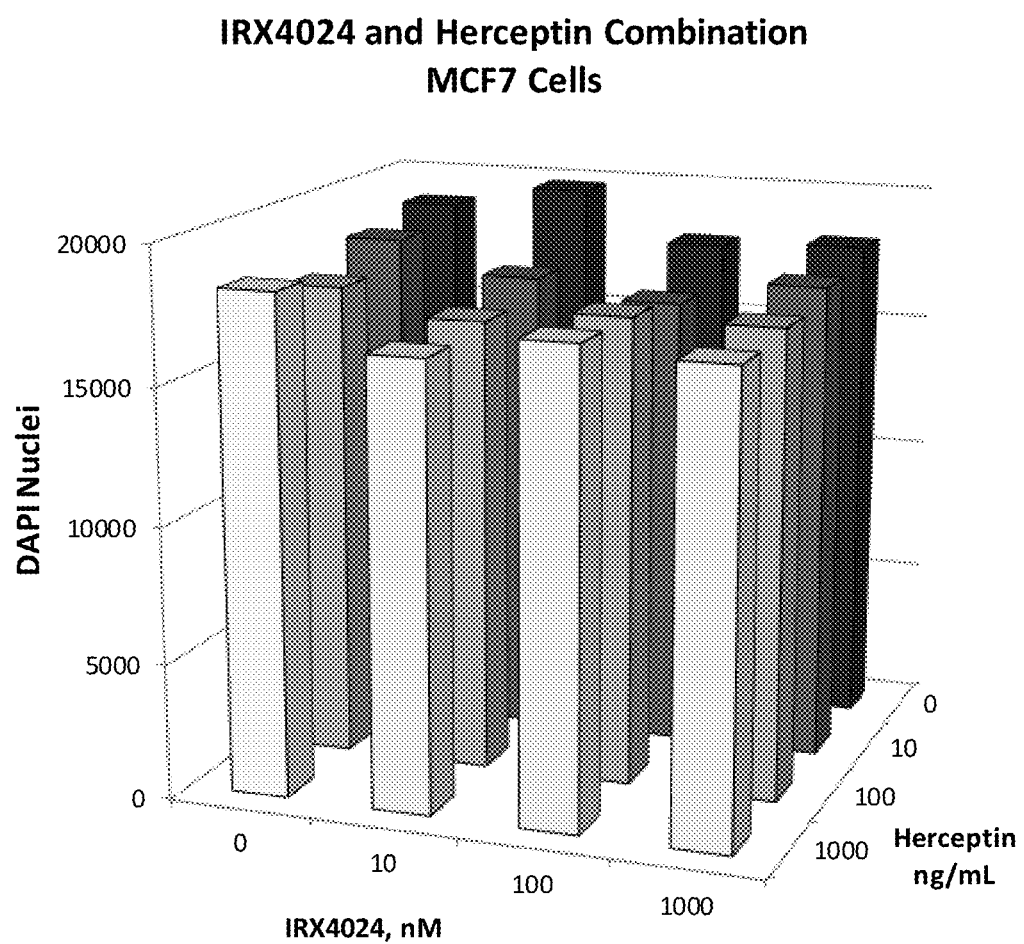
FIGS. 1A-B are three-dimensional plots depicting the growth inhibitory effects of IRX4204 and trastuzumab, alone and in combination, on breast cancer cell lines: MCF7 cells (FIG. 1A) and SkBr3 cells (FIG. 1B).

The herein disclosed embodiments include methods of treating Her2$^+$ cancers, such as Her2$^+$ carcinoma of the breast, with a combination a retinoid X (rexinoid) receptor (RXR) agonist and a Her2-targeted anticancer agent. Some embodiment further comprise administration of thyroid hormone in conjunction with the RXR agonist. Embodiments include a RXR agonist for use in combination with a Her2-targeted anticancer agent, or a thyroid hormone and a Her2-targeted anticancer agent, in the treatment of Her2$^+$ cancers. In some embodiments the Her2$^+$ cancer is Her2$^+$ breast cancer.

The methods of treatment involve the administration of a combination of two, three, or more therapeutic agents. Moreover, the administration of one of these agents may be described as being done in coordination or conjunction with another of these agents. By such combination, or administration of in coordination or in conjunction with, it is meant that the manner of administration of each of these agents is such that the physiologic effects of the agents overlap in time. This does not require that the agents be contained in the same composition or formulation, or that they be administered as separate compositions at the same time, by the same route of administration, or on the same schedule, though in some embodiments any of the foregoing may be the case. Indeed, while it is possible to administer RXR agonists, thyroid hormone, and Her2 kinase inhibitors on a daily schedule, antibodies are more typically administered at intervals measured in weeks.

Among the earlier successful targeted cancer therapies are those targeting human epidermal growth factor receptor 2 (Her2). Her2-targeted treatments include monoclonal antibodies (mAbs), such as trastuzumab and pertuzumab, and inhibitors of Her2 kinase activity, such as lapatinib, neratinib, and afatinib (which all also inhibit epidermal growth factor receptor (EGFR)). The rexinoid IRX4204 has shown activity against a variety of cancers in model systems (see for example, U.S. Patent Pub. 2008-0300312, which is incorporated herein by reference in its entirety for all that it teaches about the use of RXR agonists for the treatment of cancer) especially when used in combination with thyroid hormone (see for example, U.S. Patent Pub. 2008-0300312, which is incorporated herein by reference in its entirety for all that it teaches about the use of RXR agonists for the treatment of cancer). It is disclosed herein that the combination of IRX4204 and a Her2-targeted therapeutic agent are particularly effective against Her2$^+$ cancers, such as Her2$^+$ breast cancer. Thus various embodiments are combinations of IRX4204 and a Her2-targeted therapeutic agent, and methods of treatment involving administration of both IRX4204 and a Her2-targeted therapeutic agent. Some embodiments further include thyroid hormone or the administration of thyroid hormone. Other embodiments exclude thyroid hormone or the administration of thyroid hormone.

A Her2-targeted therapeutic agent as used herein is a therapeutic agent that inhibits growth of cancer cells by inhibiting Her2 function. Such agents include mAbs that bind to Her2, antibody-drug conjugates comprising such mAbs, and inhibitors of Her2 tyrosine kinase activity. Collectively, such agents can be referred to as means for therapeutically targeting Her2. Some embodiments specifically include or are limited to one or more of these classes of agent, or one or more species within one or more of these classes of agent. Some embodiments specifically exclude one or more of these classes of agent, or one or more species within one or more of these classes of agent. Thus, means for therapeutically targeting Her2 are mAbs that bind to Her2, antibody-drug conjugates comprising mAbs that bind to Her2, and inhibitors or Her2 tyrosine kinase activity. In some embodiments, the mAb in an antibody-drug conjugate has therapeutic activity by itself, in other embodiments it does not.

Many embodiments comprise administration of a single anti-Her2 mAb, but some embodiments comprise administration of multiple anti-Her2 mAbs, for example, trastuzumab and pertuzumab. While the disclosed embodiments are generally described as using anti-Her2 mAbs, further embodiments can substitute anti-Her2 polyclonal antiserum for anti-Her2 mAb. Some embodiments can comprise administration of additional mAbs targeting other antigens, some embodiments specifically exclude administration of other antibodies.

Anti-Her2 Antibodies

Her2 is a growth factor receptor found on, and implicated in, a variety of cancers, especially breast cancer but also, for example, gastroesophageal cancer, ovarian cancer, stomach cancer, adenocarcinoma of the lung, uterine cancer (such as serous endometrial carcinoma), or salivary duct carcinoma. Anti-Her2 antibodies are believed to work as anticancer agents through a combination of mechanisms: inhibition of signaling through Her2, antibody-dependent cellular cytotoxicity (ADCC), and mediating presentation of tumor antigen by antigen presenting cells (APC), such as macrophages; additional mechanisms may also exist. The best understood and most clinically advanced anti-Her2 antibodies are trastuzumab, pertuzumab, and margetuximab.

In some embodiments, these antibodies are administered by intravenous infusion. In exemplary embodiments infusions may be done over 30-90 minutes and may occur at intervals of 1-3 weeks for as long as a year. In some such embodiments, the antibody is administered at an initial higher dose and a subsequent lower dose. In some such embodiments, the initial higher dosage is twice the subsequent lower dosage. In some such embodiments, the initial dose is single administration. In other such embodiments the initial dosage is administered multiple times before switching to the lower subsequent dosage. Specific examples of dosages and dose regimens can be found in the prescribing information for HERCEPTIN® and PERJETA®, which are incorporated herein by reference in their entireties.

Trastuzumab (sold as HERCEPTIN®) binds to domain IV of the extracellular segment of Her2. Trastuzumab inhibits the proliferation of cells that overexpress Her2 and mediates ADCC. Biosimilar antibodies to trastuzumab have been developed and are marketed in some jurisdictions.

Pertuzumab (sold as PERJETA®) recognizes the extracellular dimerization domain (domain II) of Her2, a different epitope than trastuzumab. By preventing ligand dependent dimerization, it inhibits signaling through Her2, leading to cell growth arrest and apoptosis. Pertuzumab also mediates ADCC. Pertuzumab augmented the activity of trastuzumab in tumor xenograft models that over express Her2.

Margetuximab (currently still in clinical development) recognizes the same epitope as trastuzumab, but possesses an engineered Fc region designed to increase Fc-dependent mechanisms of immune attack, such as ADCC. The engineered Fc region confers increased binding to activating Fc-γ receptors (CD16A) and reduced binding to inhibitory Fc-γ receptors (CD16B) on immune effector cells, including monocytes, macrophages, dendritic cells and natural killer (NK) cells.

Further anti-Her2 mAbs include TrasGEX®, HM2, hertuzumab, and HT-19, TrasGEX® and HM2 are being developed as "biobetters" of trastuzumab, while the other two are independently derived. In HM2 a metal-binding motif has been incorporated into trastuzumab to aid conjugation. TrasGEX® is a glycosylation-optimized version of trastuzumab. Hertuzumab had a higher ELISA-based affinity for Her2 than trastuzurnab. HT-19 is an IgG1 antibody that is non-competitive for HER2 binding with trastuzumab and pertuzumab; that is, it binds a different epitope than either of those two mAbs.

Many embodiments comprise administration of a single anti-Her2 mAb, but some embodiments comprise administration of multiple anti-Her2 mAbs, for example, trastuzumab and pertuzumab. While the disclosed embodiments are generally described as using anti-Her2 mAbs, further embodiments can substitute anti-Her2 polyclonal antiserum for anti-Her2 mAb.

Antibody-Drug Conjugates

In addition to use of anti-Her2 mAbs themselves as therapeutic agents, anti-Her2 mAbs have also been incorporated into antibody-drug conjugates. One example is ado-trastuzumab emtansine (sold as KADCYLA®). Further examples include A166, ALT-P7 (trastuzumab biobetter HM2 conjugated in a site-specific manner to monomethyl auristatin E), ARX788 (a monoclonal HER2 targeting antibody site-specifically conjugated, via a non-natural amino acid linker para-acetyl-phenylalanine (pAcF), to monomethyl auristatin F), DHES0815A (a monoclonal HER-2 targeting antibody linked to pyrrolo[2,1-c][1,4]benzodiazepine monoamide), DS-8201a (trastuzumab deruxtecan; trastuzumab, an enzymatically cleavable maleimide glycyn-glycyn-phenylalanyn-glycyn (GGFG) peptide linker and a topoisomerase I inhibitor, fam-trastuzumab deruxtecan (sold as ENHERTU®), RC48 (humanized anti-HER2 antibody hertuzumab conjugated with monomethyl auristatin E (MMAE) via a cleavable linker), SYD985 (([vic-]trastuzumab duocarmazine; trastuzumab linked via a cleavable valine-citrulline peptide to the synthetic duocarmycin analog seco DUocarmycin hydroxyBenzamide Azaindole), MED14276 (HER2-bispecific antibody targeting two different epitopes on HER2, site-specifically conjugated via a maleimidocaproyl linker to the potent tubulysin-based microtubule inhibitor AZ13599185) and XMT-1522 (TAK-522; HT-19 conjugated with the DOLAFLEXIN® platform to auristatin F-hydroxypropylamide).

In some embodiments, the Her2-targeting component comprises, or is, an antibody-drug conjugate comprising an anti-Her2 antibody.

Her2 Kinase Inhibitors

Her2 and EGFR are closely related protein tyrosine kinases and many drugs developed as an inhibitor of one also inhibit the other. At least four drugs that are irreversible inhibitors of these kinases are now marketed as a cancer treatment, though the indications vary: lapatinib, neratinib, afatinib, and dacomitinib. It should be noted that not all EGFR inhibitors are irreversible inhibitors or are known to cross-inhibit Her2. EGFR inhibitors that do not—or are not known to—inhibit Her2 should not be considered Her2 inhibitors as the term is used herein. In some embodiments, the Her2 inhibitor is an irreversible inhibitor. In some embodiments, the Her2 inhibitor is not a reversible inhibitor.

Lapatinib (sold as TYKERB®) (CAS No. 231277-92-2), typically provided as Lapatinib Ditosylate (CAS No. 388082-77-7) or the monohydrate thereof, can be administered, according to its prescribing instructions which are incorporated herein by reference in their entirety, on a 21 day treatment cycle, at 1250 or 1500 mg once daily, depending on indication. Lapatinib plus capecitabine is taken on days 1 to 14. Lapatinib alone is taken on days 15 to 21. At the end of the 21 days, the treatment cycle should be repeated until disease progression or unacceptable toxicity occurs. Capecitabine is administered orally in two doses approximately 12 hours apart at a dosage of 2000 mg/m$^2$/day.

Neratinib (sold as NERLYNX®) (CAS No. 698387-09-6) can be administered, according to its prescribing instructions which are incorporated herein by reference in their entirety, with food at an initial dose of 240 mg/day and taken daily for a year. If toxicity exceeds grade 1, the dose can be reduced by 40 mg/day in stepwise fashion until toxicity is grade 1 or less. If the dose has been reduced to 120 mg/day and toxicity remains greater than grade 1, treatment with Neratinib should be discontinued.

Afatinib (sold as GILOTRIF®) (CAS No. 850140-72-6) can be administered, according to its prescribing instructions which are incorporated herein by reference in their entirety, orally without food once daily at 40 mg/day until disease progression or no longer tolerated by the patient.

Dacomitinib (sold as VIZIMPRO®) (CAS No. 1110813-31-4) can be administered, according to its prescribing instructions which are incorporated herein by reference in their entirety, orally with or without food, once daily at 45 mg/day until disease progression or unacceptable toxicity occurs. Upon occurrence of unacceptable toxicity, the dosage can be reduced in stepwise fashion to 30 or 15 mg/day.

Tucatinib (sold as TUKYSA®) (CAS No. 937263-43-9) can be administered, according to its prescribing instructions which are incorporated herein by reference in their entirety, orally with or without food, 300 mg twice daily (12 hours apart) in combination with trastuzumab and capecitabine until disease progression or unacceptable toxicity. Upon occurrence of unacceptable toxicity, the dosage can be reduced in stepwise fashion, 50 mg per step, to 150 mg, twice daily.

The above dosing information, in addition to disclosing specific embodiments in which these Her2 kinase inhibitors may be used in combination with an RXR agonist, provides general guidance as to dosing practices with such drugs. The disclosed embodiments are not necessarily limited to these specific dosing regimens and it is within the skill of the physician to modify these regimens for individual patients. Due to the improved and synergistic effect of these drugs when used in combination with a RXR agonist, unacceptable toxicity may be avoided by use of lower dosages of the kinase inhibitor while still achieve beneficial therapeutic effect.

Other Her2 kinase inhibitors include canertinib (CAS No. 267243-28-7), sapitinib (CAS No. 848942-61-0), CP-724714 (CAS No. 537705-08-1), and CUDC-101 (CAS No. 1012054-59-9).

RXR Agonists

Preclinical studies with rexinoids suggest that selective activation of Retinoid X Receptors (RXR), which modulate functions associated with differentiation, inhibition of cell growth, apoptosis and metastasis, may be useful in treating a variety of diseases associated with the biochemical functions modulated by RXR.

The Retinoic Acid Receptors (RARs) and RXRs and their cognate ligands function by distinct mechanisms. The term "RAR" as used herein refers to one or more of RARα, RARβ, or RARγ. The term "RXR" as used herein refers to one or more of RXRα, RXRβ, or RXRγ. A RAR biomarker is a distinctive biological, biochemical or biologically derived indicator that signifies patient RAR activity. RAR biomarkers include, but are not limited to, CYP26 levels, CRBPI levels, and the like, and combinations thereof.

In some embodiments, the RAR activation threshold means one or more of a CYP26 level which is 25% increased over baseline and a CRBPI level 25% increased over baseline. The RARs form heterodimers with RXRs and these RAR/RXR heterodimers bind to specific response elements in the promoter regions of target genes. The binding of RAR agonists to the RAR receptor of the heterodimer results in activation of transcription of target genes leading to retinoid effects. On the other hand, the disclosed RXR agonists do not activate RAR/RXR heterodimers. RXR heterodimer complexes like RAR/RXR can be referred to as non-permissive RXR heterodimers as activation of transcription due to ligand-binding occurs only at the non-RXR protein (e.g., RAR); activation of transcription does not occur due to ligand binding at the RXR.

RXRs also interact with nuclear receptors other than RARs and RXR agonists may elicit some of its biological effects by binding to such RXR/receptor complexes. These RXR/receptor complexes can be referred to as permissive RXR heterodimers as activation of transcription due to ligand-binding could occur at the RXR, the other receptor, or both receptors. Examples of permissive RXR heterodimers include, without limitation, peroxisome proliferator activated receptor/RXR (PPAR/RXR), farnesyl X receptor/RXR (FXR/RXR), nuclear receptor related-1 protein (Nurr1/RXR) and liver X receptor/RXR (LXR/RXR). Alternately, RXRs may form RXR/RXR homodimers which can be activated by RXR agonists leading to rexinoid effects. Also, RXRs interact with proteins other than nuclear receptors and ligand binding to an RXR within such protein complexes can also lead to rexinoid effects. Due to these differences in mechanisms of action, RXR agonists and RAR agonists elicit distinct biological outcomes and even in the instances where they mediate similar biological effects, they do so by different mechanisms. Moreover, the unwanted side effects of retinoids, such as pro-inflammatory responses or mucocutaneous toxicity, are mediated by activation of one or more of the RAR receptor subtypes. Stated another way, biological effects mediated via RXR pathways would not induce pro-inflammatory responses, and thus, would not result in unwanted side effects.

Thus, aspects of the present specification provide, in part, a RXR agonist. As used herein, the term "RXR agonist", is synonymous with "selective RXR agonist" and refers to a compound that selectively binds to one or more RXR receptors like a RXRα, a RXRβ, or a RXRγ in a manner that elicits gene transcription via an RXR response element. As used herein, the term "selectively binds," when made in reference to a RXR agonist, refers to the discriminatory binding of a RXR agonist to the indicated target receptor like a RXRα, a RXRβ, or a RXRγ such that the RXR agonist does not substantially bind with non-target receptors like a RARα, a RARβ or a RARγ. In some embodiments, the term "RXR agonist" includes esters of RXR agonist.

For each of the herein disclosed embodiments the RXR agonists can be compounds having the structure of Formula I

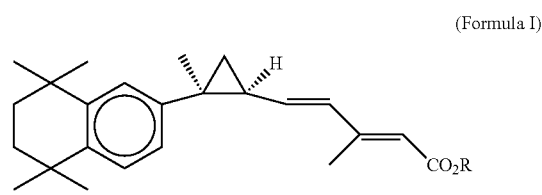

(Formula I)

wherein R is H, or lower alkyl of 1 to 6 carbons; or the agonist is a pharmaceutically acceptable salt of the compounds.

Also disclosed herein are esters of RXR agonists. An ester may be derived from a carboxylic acid of C1, or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, isobutyl, t-butyl, pentyl isomers, hexyl isomers, cyclopropyl, cyclobutyl, cyclopentyl, cyclohexyl, and combinations thereof having from 1-6 carbon atoms, etc. In some embodiments the RXR agonist is the ethyl ester of formula I.

In some embodiments the RXR agonist is 3,7-dimethyl-6(S),7(S)-methano,7-[1,1,4,4-tetramethyl-1,2,3,4-tetrahydron-aphth-7-yl]2(E), 4(E) heptadienoic acid, also known as IRX4204, and has the following chemical structure:

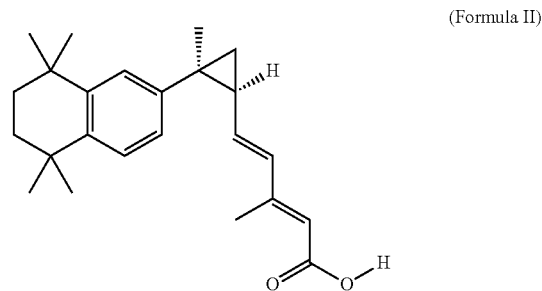

(Formula II)

Pharmaceutically acceptable salts of RXR agonists can also be used in the disclosed embodiments. Compounds disclosed herein which possess a sufficiently acidic, a sufficiently basic, or both functional groups, and accordingly can react with any of a number of organic or inorganic bases, and inorganic and organic acids, to form a salt.

Acids commonly employed to form acid addition salts from RXR agonists with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, di nitrobenzoate, hydroxybenzoate, methoxybenzoate, phthalate, sulfonate, xylenesulfonate, phenylacetate, phenylpropionate, phenyl butyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Bases commonly employed to form base addition salts from RXR agonists with acidic groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tertbutylamine, or tris-(hydroxymethyl)methylamine, N,N-dilower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

IRX4204, like some other RXR ligands, does not activate non-permissive heterodimers such as RAR/RXR. However, IRX4204, is unique in that it specifically activates the Nurr1/RXR heterodimer and does not activate other permissive RXR heterodimers such as PPAR/RXR, FXR/RXR, and LXR/RXR. Other RXR ligands generally activate these permissive RXR heterodimers. Thus, all RXR ligands cannot be classified as belonging to one class. IRX4204 belongs to a unique class of RXR ligands which specifically activate RXR homodimers and only one of the permissive RXR heterodimers, namely the Nurr1/RXR heterodimer.

In one embodiment, the selective RXR agonist does not activate to any appreciable degree the permissive heterodimers PPAR/RXR, FXR/RXR, and LXR/RXR. In another embodiment, the selective RXR agonist, activates the permissive heterodimer Nurr1/RXR. One example of such a selective RXR agonist is 3,7-dimethyl-6(S),7(S)-methano, 7-[1,1,4,4-tetramethyl-1,2,3,4-tetrahydronaphth-7-yl]2(E),4 (E) heptadienoic acid (IRX4204) disclosed herein, the structure of which is shown in Formula II. In other aspects of this embodiment, the RXR agonists activates the permissive heterodimers PPAR/RXR, FXR/RXR, or LXR/RXR by 1% or less, 2% or less, 3% or less, 4% or less, 5% or less, 6% or less, 7% or less, 8% or less, 9% or less, or 10% or less relative to the ability of activating agonists to the non-RXR receptor to activate the same permissive heterodimer. Examples of RXR agonists, which activates one or more of PPAR/RXR, FXR/RXR, or LXR/RXR include LGD1069 (bexarotene) and LGD268.

Binding specificity is the ability of a RXR agonist to discriminate between a RXR receptor and a receptor that does not contain its binding site, such as a RAR receptor.

Particular embodiments provide methods of treating cancer comprising administering to a patient in need of such treatment a RXR agonist at a level below an RAR activating threshold and at or above an RXR activating threshold.

For IRX4204, the RAR $EC_{10}$ (the concentration effective to cause a 10% of maximal activation of the RAR) is 300 nM for the α isoform and 200 nM for the β and γ isoforms. Thus, in some embodiments, concentrations not exceeding 200 nM are considered to be below an RAR activating concentration. For IRX4204, the RXR $EC_{90}$ (the concentration effective to cause a 90% of maximal activation of the RXR) is 0.1 nM for the α and γ isoforms and 1 nM for the isoform. Thus, in some embodiments concentrations of at least 0.1 nM are considered to be above an RXR activating threshold. Based on studies in humans, oral dosages of IRX4204 of 20 mg/m$^2$/day will produce systemic concentrations that remain below 200 nM. Similarly, it is estimated that an oral dosage in the range of 0.01 to 0.02 mg/m$^2$/day will produce systemic concentrations of 0.1 nM or greater. Thus, in various individual embodiments a dosage of IRX4204 is at least 0.01, 0.02, 0.03, 0.05, 0.1, 0.3, 0.5, 1, 3 or 5 mg/m$^2$/day and does not exceed 150, 200, or 300 mg/m$^2$/day, or any range bound by a pair of these values.

In other embodiments, the dosage for a human adult of the RXR agonist, for example IRX4204, is from 0.2 to 300 mg/day, such as in individual embodiments, from 0.5, 1, 2, 3, 4, 5, 6, 7, 8, 9, or 10 mg/day, but not to exceed 10, 15, 20, 50, or 100 mg/day, or any range bound by a pair of these values.

The RXR agonist can be administered to a mammal using standard administration techniques, including parenteral, oral, intravenous, intraperitoneal, subcutaneous, pulmonary, transdermal, intramuscular, intranasal, buccal, sublingual, or suppository administration. The term "parenteral," as used herein, includes intravenous, intramuscular, subcutaneous, rectal, vaginal, and intraperitoneal administration. The RXR agonist preferably is suitable for oral administration, for example as a pill, tablet or capsule. Administration may be continuous or intermittent. In certain embodiments, the total daily dosage of RXR agonist can be administered as a single dose or as two doses administered with a 24 hour period spaced 8 to 16, or 10 to 14, hours apart.

Thyroid Hormone

Both biologically sourced and synthetic thyroid hormones have been used in medicine. The major forms of thyroid hormone are referred to a $T_3$ (triiodothyronine) and $T_4$ (thyroxine). Thyroxine is less active but has a longer half-life and is sometimes considered a prohormone of triiodothyronine. As used herein, the term "thyroid hormone" refers to thyroxine and triiodothyronine. Thyroxine (thyroid hormone $T_4$, levothyroxine sodium) is a tyrosine-based hormone produced by the thyroid gland and is primarily responsible for regulation of metabolism. Both have wide commercial availability and are suitable for use in the herein disclosed embodiments. However, the synthetic form of $T_4$, levothyroxine, is much more commonly utilized (except in patients unable to convert $T_4$ into $T_3$) as its longer half-life in the body facilitates once-daily administration. In some embodiments, the administered thyroid hormone is specifically thyroxine. In some embodiments, the administered thyroid hormone is triiodothyronine.

Administration of RXR agonists, or esters thereof, may lead to the suppression of serum thyroid hormones and possibly to clinical hypothyroidism and related conditions.

However, in some embodiments thyroid hormone is not co-administered (or is not primarily co-administered) to remediate a suppression of serum thyroid hormone levels. Co-administration of thyroid hormone with an RXR agonist improves the RXR agonist's anti-cancer efficacy, as compared to the effect of the RXR agonist alone, likely through multiple mechanisms of action. The co-administered thyroid hormone can also mitigate the hypothyroid-inducing effects of the RXR agonist, thereby improving the clinical safety and tolerability of the treatment. Thus, in preferred embodiments, thyroid hormone is co-administered with an RXR agonist to improve the efficacy of the treatment, whether or not administration of the RXR agonist has caused, or is expected to cause, clinical hypothyroidism. By administration of thyroid hormone in coordination or in conjunction with the RXR agonist it is meant that the manner of administration of each of these two agents is such that the physiologic effects of the two agents overlap in time. This does not require that the RXR agonist and thyroid hormone be contained in the same composition or formulation, or that they be administered as separate compositions at the same time, by the same route of administration, or on the same schedule, though in some embodiments any of the foregoing may be the case.

Suitable thyroxine doses are generally from about 5 μg/day to about 250 μg/day orally initially with an increase in dose every 2-4 weeks as needed. In other embodiments, the suitable thyroxine dose is from about 5 μg/day to about 225 μg/day, from about 7.5 μg/day to about 200 μg/day, from about 10 μg/day to about 175 μg/day, from about 12.5 μg/day to about 150 μg/day, from about 15 μg/day to about 125 μg/day, from about 17.5 μg/day to about 100 μg/day, from about 20 μg/day to about 100 μg/day, from about 22.5 μg/day to about 100 μg/day, from about 25 μg/day to about 100 μg/day, from about 5 μg/day to about 200 μg/day, from about 5 μg/day to about 100 μg/day, from about 7.5 μg/day to about 90 μg/day, from about 10 μg/day to about 80 μg/day, from about 12.5 μg/day to about 60 μg/day, or from about 15 μg/day to about 50 μg/day. Increases in dose are generally made in increments of about 5 μg/day, about 7.5 μg/day, about 10 μg/day, about 12.5 μg/day, about 15 μg/day, about 20 μg/day, or about 25 μg/day. In certain embodiments, the suitable thyroid hormone dose is a dose able to produce serum levels of $T_4$ in the top 50%, the top 60%, the top 70%, the top 80%, or the top 90% of the normal range for the testing laboratory. As the normal range of $T_4$ levels may vary by testing laboratory, the target $T_4$ levels are based on normal ranges determined for each particular testing laboratory.

For each embodiment involving a combination of RXR agonist and Her2-targeting therapeutic agent, there is a parallel embodiment in which the combination further comprises thyroid hormone.

Pharmaceutical Compositions and Formulations

The various component active agents used in the herein described treatments will typically exist as pharmaceutical compositions or formulations. Such compositions or formulations may be a liquid formulation, semi-solid formulation, or a solid formulation. A formulation disclosed herein can be produced in a manner to form one phase, such as, e.g., an oil or a solid. Alternatively, a formulation disclosed herein can be produced in a manner to form two phases, such as, e.g., an emulsion. A pharmaceutical composition disclosed herein intended for such administration may be prepared according to any method known to the art for the manufacture of pharmaceutical compositions.

Liquid formulations suitable for parenteral injection or for nasal sprays may comprise physiologically acceptable sterile aqueous or nonaqueous solutions, dispersions, suspensions or emulsions and sterile powders for reconstitution into sterile injectable solutions or dispersions. Formulations suitable for nasal administration may comprise physiologically acceptable sterile aqueous or nonaqueous solutions, dispersions, suspensions or emulsions. Examples of suitable aqueous and nonaqueous carriers, diluents, solvents or vehicles include water, ethanol, polyols (propylene glycol, polyethyleneglycol (PEG), glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

A pharmaceutical composition disclosed herein can optionally include a pharmaceutically acceptable carrier that facilitates processing of an active compound into pharmaceutically acceptable compositions. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. (This definition is also application to the phrase "pharmaceutically-acceptable salts"). As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary, or excipient." Such a carrier generally is mixed with an active compound or permitted to dilute or enclose the active compound and can be a solid, semi-solid, or liquid agent. It is understood that the active compounds can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active compound, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, $7^{th}$ ed. 1999); Remington: The Science and Practice of Pharmacy (Alfonso R. Gennaro ed., Lippincott, Williams & Wlkins, $20^{th}$ ed. 2000); Goodman & Gilman's The Pharmacological Basis of Therapeutics (Joel G. Hardman et al., eds., McGraw-Hill Professional, $10^{th}$ ed. 2001); and Handbook of Pharmaceutical Excipients (Raymond C. Rowe et al., APhA Publications, 4th edition 2003). These protocols are routine and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, borate buffers, citrate buffers, phosphate buffers, neutral buffered saline, and phosphate buffered saline. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole, and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., sodium chlorite and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

Pharmaceutical formulations suitable for administration by inhalation include fine particle dusts or mists, which may be generated by means of various types of metered, dose pressurized aerosols, nebulizers, or insufflators.

Semi-solid formulations suitable for topical administration include, without limitation, ointments, creams, salves, and gels. In such solid formulations, the active compound may be admixed with at least one inert customary excipient (or carrier) such as, a lipid and/or polyethylene glycol.

Solid formulations suitable for oral administration include capsules, tablets, pills, powders and granules. In such solid formulations, the active compound may be admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

The small molecule components of the various embodiments, that is, the RXR agonist, thyroid hormone, and Her2 kinase inhibitors are capable of being formulated in solid, oral dosage forms. The antibody components are generally formulated as liquids typically for intravenous infusion. In alternative embodiments the antibody components may be supplied in lyophilized form for reconstitution as a liquid locally at the site of treatment, where they are also typically infused intravenously into the patient. While intravenous infusion is typical, in alternative embodiments the antibody may be administered by another route of administration, such as subcutaneous injection or infusion.

Treatment

As used herein, the terms "treatment," "treating," and the like refer to obtaining a desired pharmacologic and/or physiologic effect. This may be observed directly as a slowing of tumor growth, stabilization of disease, or a partial or complete response (that is, tumor regression or elimination of tumors), or extended overall or disease-free survival. Treatment may also be observed as an amelioration or reduction of symptoms related to the underlying cancer. However, as cancer treatment, the disclosed embodiments' aim and mechanism is directed to inhibiting, stabilizing, or reducing tumor growth (including metastases), or partially or completely eliminating tumors, or extending overall or disease-free survival; effects on other cancer symptoms are secondary. Direct treatment of such other symptoms (for example, pain, nausea, loss of appetite, etc.) is not within the scope of treating cancer as used herein. That is, treating a symptom, for example, cachexia in a cancer patient is not treating cancer. However, an agent that treats cancer (e.g., has an impact on the growth and/or spread of cancer) may also ameliorate a symptom, such as cachexia, either indirectly, through its effect on the cancer, or directly, through a pleiotropic effect. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the Her2-targeted therapy, RXR agonist, and if used, thyroid hormone, to elicit a desired response in the individual.

However, the dose administered to a mammal, particularly a human, in the context of the present methods, should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Treatment activity includes the administration of the medicaments, dosage forms, and pharmaceutical compositions described herein to a patient, especially according to the various methods of treatment disclosed herein, whether by a healthcare professional, the patient his/herself, or any other person. Treatment activities include the orders, instructions, and advice of healthcare professionals such as physicians, physician's assistants, nurse practitioners, and the like that are then acted upon by any other person including other healthcare professionals or the patient his/herself. In some embodiments, treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used—by a policy or practice standard as might be established by a hospital, clinic, health maintenance organization, medical practice or physicians group, and the like.

To benefit from the combined effect of a RXR agonist of Formula I (or pharmaceutically acceptable salt thereof) and Her2-targeted therapeutics, embodiments include methods of treatment comprising or consisting of administering RXR agonist of Formula I (or pharmaceutically acceptable salt thereof) and a Her2-targeted therapeutic to a patient having a Her2$^+$ cancer. Some embodiments further comprise administration of thyroid hormone in coordination with administration of the RXR agonist. In some embodiments the Her2$^+$ cancer is a Her2$^+$ breast cancer. In some embodiments the Her2$^+$ cancer is a Her2$^+$ gastroesophageal cancer, ovarian cancer, stomach cancer, adenocarcinoma of the lung, uterine cancer (such as serous endometrial carcinoma), or salivary duct carcinoma. Some embodiments specifically include one or more of these cancers. Other embodiments specifically exclude one or more of these cancers.

In various embodiments the herein disclosed treatments may be applied as a primary therapy, as a debulking therapy prior to surgical removal of tumor, or as an adjuvant therapy subsequent to any mode of primary therapy (especially surgery) to address residual disease and/or lower the risk of recurrent cancer.

In some embodiments the patient having a Her2$^+$ cancer has not been previously treated with either RXR agonist of Formula I (or pharmaceutically acceptable salt thereof) or a Her2-targeted therapeutic. In some embodiments the patient has been previously treated with RXR agonist of Formula I (or pharmaceutically acceptable salt thereof) and has achieved stable disease or a partial response (in some embodiments, as defined by RECIST or iRECIST criteria)—that is, the cancer is sensitive to RXR agonist of Formula I (or pharmaceutically acceptable salt thereof)—and a Her2-targeted therapeutic is added to the treatment regimen. In some embodiments the patient has been previously treated with a Her2-targeted therapeutic and has achieved stable disease or a partial response (in some embodiments, as defined by RECIST or iRECIST criteria)—that is, the cancer is sensitive to a Her2-targeted therapeutic—and RXR agonist of Formula I (or pharmaceutically acceptable salt thereof) is added to the treatment regimen.

Thus some embodiments entail administration of an RXR agonist to a patient with a Her2$^+$ tumor who has received, is receiving, or is scheduled to receive, a Her2-targeted therapeutic agent. Some embodiments entail administration of an RXR agonist to a patient in whom a Her2-targeted therapeutic agent has had some therapeutic effect (less than a complete response), that is administration of the RXR agonist is added to the therapeutic regimen for the Her2-targeted therapeutic agent. Some embodiments entail administration of a Her2-targeted therapeutic agent to a patient in whom an RXR agonist (or RXR agonist in conjunction with thyroid hormone) has had some therapeutic effect (less than a complete response), that is administration of the Her2-targeted therapeutic agent is added to the therapeutic regimen for the RXR agonist.

Therapeutic efficacy can be monitored by periodic assessment of treated patients. For repeated administrations over several days or longer, the treatment can be repeated until a desired suppression of disease or disease symptoms occurs. However, other dosage regimens may be useful and are within the scope of the present disclosure. Antibodies typically have a much longer half-life in the body than the other active agents used in these methods and therefore there will typically be substantially longer intervals (measured in weeks) between administrations.

The effectiveness of cancer therapy is typically measured in terms of "response." The techniques to monitor responses can be similar to the tests used to diagnose cancer such as, but not limited to:

A lump or tumor involving some lymph nodes can be felt and measured externally by physical examination.

Some internal cancer tumors will show up on an x-ray or CT scan and can be measured with a ruler.

Blood tests, including those that measure organ function can be performed.

A tumor marker test can be done for certain cancers.

Regardless of the test used, whether blood test, cell count, or tumor marker test, it is repeated at specific intervals so that the results can be compared to earlier tests of the same type.

Response to cancer treatment is defined several ways:

Complete response—all of the cancer or tumor disappears; there is no evidence of disease. Expression level of tumor marker (if applicable) may fall within the normal range.

Partial response—the cancer has shrunk by a percentage but disease remains. Levels of a tumor marker (if applicable) may have fallen (or increased, based on the tumor marker, as an indication of decreased tumor burden) but evidence of disease remains.

Stable disease—the cancer has neither grown nor shrunk; the amount of disease has not changed. A tumor marker (if applicable) has not changed significantly.

Disease progression—the cancer has grown; there is more disease now than before treatment. A tumor marker test (if applicable) shows that a tumor marker has risen.

Other measures of the efficacy of cancer treatment include intervals of overall survival (that is time to death from any cause, measured from diagnosis or from initiation of the treatment being evaluated)), cancer-free survival (that is, the length of time after a complete response cancer remains undetectable), and progression-free survival (that is, the length of time after disease stabilization or partial response that resumed tumor growth is not detectable).

There are two standard methods for the evaluation of solid cancer treatment response with regard to tumor size (tumor burden), the WHO and RECIST standards. These methods measure a solid tumor to compare a current tumor with past measurements or to compare changes with future measurements and to make changes in a treatment regimen. In the WHO method, the solid tumor's long and short axes are measured with the product of these two measurements is then calculated; if there are multiple solid tumors, the sum of all the products is calculated. In the RECIST method, only the long axis is measured. If there are multiple solid tumors, the sum of all the long axes measurements is calculated. However, with lymph nodes, the short axis is measured instead of the long axis. There is also a variation of the RECIST method for immunotherapies (iRECIST) which takes into account distinctive behaviors linked to these types of therapeutics, such as delayed responses after pseudoprogression. Both the RECIST 1.1 guidelines and the iRecist guidelines are incorporated by reference herein in their entirety.

In some embodiments of the herein disclosed methods, the tumor burden of a treated patient is reduced by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 1-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 5-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In other embodiments, the 10-year survival rate of treated subjects is increased by about 5%, about 10%, about 15%, about 20%, about 25%, about 30%, about 35%, about 40%, about 45%, about 50%, about 55% about 60%, about 65%, about 70%, about 75%, about 80%, about 90%, about 95%, about 100%, or any range bound by these values.

In yet other embodiments, the subject has a sustained remission of at least 6 months, at least 7 months, at least 8 months, at least 9 months, at least 10 months, at least 11 months, at least 12 months, at least 14 months, at least 16 months, at least 18 months, at least 20 months, at least 22 months, at least 24 months, at least 27 months, at least 30 months, at least 33 months, at least 36 months, at least 42 months, at least 48 months, at least 54 months, or at least 60 months or more.

In other embodiments, the methods may additionally help to treat or alleviate conditions, symptoms, or disorders related to cancer. In some embodiments, these conditions or symptoms may include, but are not limited to, anemia, asthenia, cachexia, Cushing's Syndrome, fatigue, gout, gum disease, hematuria, hypercalcemia, hypothyroidism, internal bleeding, hair loss, mesothelioma, nausea, night sweats, neutropenia, paraneoplastic syndromes, pleuritis, polymyalgia rheumatica, rhabdomyolysis, stress, swollen lymph nodes, thrombocytopenia, Vitamin D deficiency, or weight loss. While a cancer treatment may reduce or treat associated symptoms, treating symptoms associated with cancer, is not treating cancer if there is no expectation that tumor will be reduced or eliminated or their growth or spread will be inhibited.

Toxicities and adverse events are sometimes graded according to a 5 point scale. A grade 1 or mild toxicity is asymptomatic or induces only mild symptoms; may be characterized by clinical or diagnostic observations only; and intervention is not indicated. A grade 2 or moderate toxicity may impair activities of daily living (such as preparing meals, shopping, managing money, using the telephone, etc.) but only minimal, local, or non-invasive interventions are indicated. Grade 3 toxicities are medically significant but not immediately life-threatening; hospitalization or prolongation of hospitalization is indicated; activities of daily living related to self-care (such as bathing, dressing and undressing, feeding oneself, using the toilet, taking medications, and not being bedridden) may be impaired. Grade 4 toxicities are life-threatening and urgent intervention is indicated. Grade 5 toxicity produces an adverse event-related death. Thus in various embodiments, use of an RXR agonist, or RXR agonist and thyroid hormone, reduces the grade of a toxicity that would otherwise be associated with use of the Her2-targeted therapy, by allowing a lower dose to be used without substantial sacrifice of efficacy. In some embodiments, use of an RXR agonist, or RXR agonist and thyroid hormone, in combination with the Her2-targeted therapeutic agent limits a toxicity to grade 1 or less, or produces no observation of the toxicity, without substantial reduction of efficacy as would be expected from the Her2-targeted therapeutic agent alone. In some embodiments, the combined use of the Her2-targeted therapeutic agent and the RXR agonist, or RXR agonist and thyroid hormone, allows continued use of the Her2-targeted therapeutic agent at a lower dosage with therapeutic effect in instances where treatment with the Her2-targeted therapeutic agent would have had to have been discontinued due to unacceptable toxicity. In some of these embodiments, the Her2-targeted therapeutic agent comprises a Her2 kinase inhibitor.

The combination of the disclosed RXR agonists and the Her2 targeted therapeutics are synergistic in effect. That is, they interact in a positive manner to produce a greater inhibition of tumor cell growth, than would be expected from the independent (non-interacting) effects of the two. Thus, some embodiments produce improved efficacy. Other embodiments allow for the reduction of dosage in order to reduce toxicity while still achieving at least similar efficacy as provided by an individual therapeutic agent. In some embodiments, both reduced toxicity and improved efficacy (as compared to the more toxic single agent) is achieved.

For each method of treatment there are further parallel embodiments related to the foregoing methods directed to use of the RXR agonist in conjunction with a Her2-targeted therapeutic agent, or a Her2-targeted therapeutic agent and thyroid hormone, to treat Her2$^+$ cancer; directed to use of the RXR agonist in the manufacture of a medicament for use in combination with a Her2-targeted therapeutic agent, or a Her2-targeted therapeutic agent and thyroid hormone, to treat Her2$^+$ cancer.

Further embodiments include a combination comprising a RXR agonist as herein described and a Her2-targeted therapeutic agent. Some embodiments further comprise a thyroid hormone. In some embodiments, the Her2-targeted therapeutic agent is an anti-Her2 antibody. In some embodiments the Her2-targeted therapeutic agent is a Her2 kinase inhibitor.

Further embodiments include kits comprising the above combinations. The kits may additionally comprise solvents, diluents, injectors, and the like that may facilitate administration of one or more of the therapeutic agents. The kits may further comprise instructions for the coordinated use of the therapeutic agents utilized in the disclosed methods, whether or not any particular agent is supplied in the kit.

LIST OF PARTICULAR EMBODIMENTS

The following listing of embodiments is illustrative of the variety of embodiments with respect to breadth, combinations and sub-combinations, class of invention, etc., elucidated herein, but is not intended to be an exhaustive enumeration of all embodiments finding support herein.

Embodiment 1

A method of treating a patient with Her2+ cancer comprising administering a RXR agonist of Formula I,

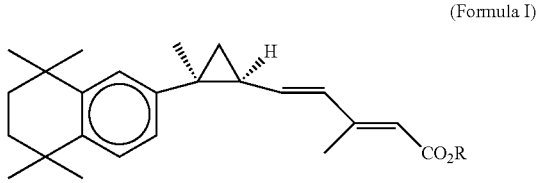

(Formula I)

wherein R is H, or lower alkyl of 1 to 6 carbons; or a pharmaceutically-acceptable salt thereof, to the patient, wherein the patient has received, is receiving, or is scheduled to receive a Her2-targeted therapeutic agent.

Embodiment 2

A method of treating a patient with Her2+ cancer comprising administering a RXR agonist of Formula I,

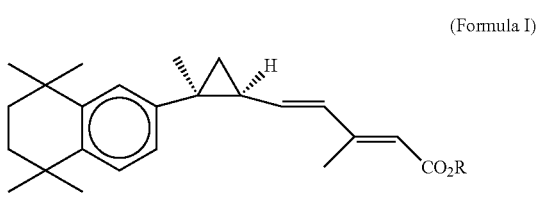

(Formula I)

wherein R is H, or lower alkyl of 1 to 6 carbons; or a pharmaceutically-acceptable salt thereof, and a Her2-targeted therapeutic agent.

Embodiment 3

A method of treating a patient with Her2+ cancer undergoing treatment with a RXR agonist of Formula I,

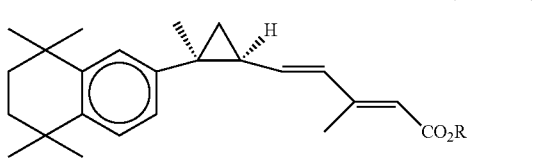

(Formula I)

wherein R is H, or lower alkyl of 1 to 6 carbons; or a pharmaceutically-acceptable salt thereof, wherein there is evidence of therapeutic effect that is less than a complete response, comprising continuing treatment with the RXR agonist and initiating treatment with a Her2-targeted therapeutic agent.

Embodiment 4

A method of treating a patient with Her2+ cancer undergoing treatment with a Her2-targeted therapeutic agent, wherein there is evidence of therapeutic effect that is less than a complete response, comprising continuing treatment with the Her2-targeted therapeutic agent and initiating treatment with a RXR agonist of Formula I,

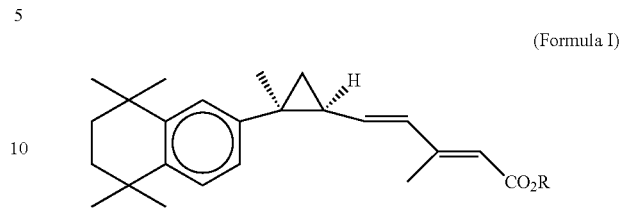

(Formula I)

wherein R is H, or lower alkyl of 1 to 6 carbons; or a pharmaceutically-acceptable salt thereof.

Embodiment 5

A method of treating a patient with Her2+ cancer comprising administering a RXR agonist of Formula I,

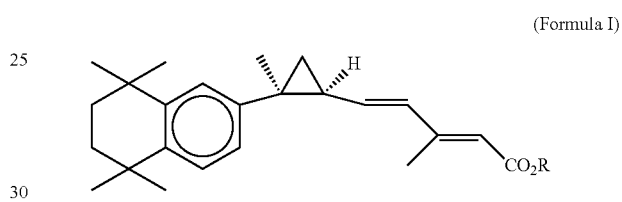

(Formula I)

wherein R is H, or lower alkyl of 1 to 6 carbons; or a pharmaceutically-acceptable salt thereof, to the patient, wherein the patient has received, is receiving, or is scheduled to receive means for therapeutically targeting Her2.

Embodiment 6

The method of Embodiment 5, wherein the means for therapeutically targeting Her2 are:
means for inhibiting Her2+ tumor cell proliferation,
means for mediating ADCC of Her2+ tumor cells,
immunoglobulin means for inhibiting Her2 signaling,
means for delivering a cytotoxic agent to Her2+ cells, or
small molecule means for inhibiting Her2 kinase activity.

Embodiment 7

A method of treating a patient with Her2+ cancer comprising administering means for activating RXR/Nurr1 heterodimeric receptors or rexinoid means for inhibiting tumor growth, wherein the patient has received, is receiving, is scheduled to receive a Her2-targeted therapeutic agent.

Embodiment 8

The method of any one of Embodiments 1-7, further comprising administering thyroid hormone in conjunction with the RXR agonist.

Embodiment 9

The method of Embodiment 8, wherein the thyroid hormone is thyroxine.

Embodiment 10

The method of any one of Embodiments 1-9, wherein the RXR agonist, the means for activating RXR/Nurr1 heterodimeric receptors, or the rexinoid means for inhibiting tumor growth, is a compound of Formula I.

Embodiment 11

The method of any one of Embodiments 1-9, wherein the RXR agonist, the means for activating RXR/Nurr1 heterodimeric receptors, or the rexinoid means for inhibiting tumor growth, is a pharmaceutically-acceptable salt of a compound of Formula I.

Embodiment 12

The method of any one of Embodiments 1-9, wherein the RXR agonist, the means for activating RXR/Nurr1 heterodimeric receptors, or the rexinoid means for inhibiting tumor growth, is a compound of Formula II

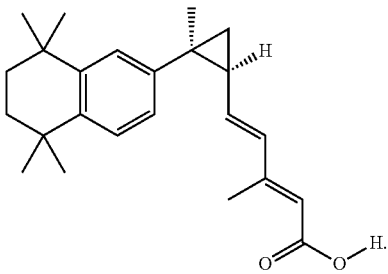

(Formula II)

Embodiment 13

The method of any one of Embodiments 1-12, wherein:
the Her2-targeted therapeutic agent,
the means for inhibiting Her2$^+$ tumor cell proliferation,
the means for mediating ADCC of Her2$^+$ tumor cells,
the immunoglobulin means for inhibiting Her2 signaling, or
the means for delivering a cytotoxic agent to Her2$^+$ cells, comprises an anti-Her2 therapeutic antibody.

Embodiment 14

The method of Embodiment 13, wherein the therapeutic antibody is trastuzumab or pertuzumab.

Embodiment 15

The method of Embodiment 13, wherein the therapeutic antibody is margetuximab, TrasGEX, HM2, hertuzumab, or HT-19

Embodiment 16

The method of any one of Embodiments 1-13, wherein the Her2-targeted therapeutic agent, the means for inhibiting Her2$^+$ tumor cell proliferation, or the immunoglobulin means for inhibiting Her2 signaling, comprises an antibody-drug conjugate wherein the antibody is an anti-Her2 antibody.

Embodiment 17

The method of Embodiment 16, wherein the antibody-drug conjugate or the means for delivering a cytotoxic agent to Her2$^+$ cells, is ado-trastuzumab emtansine.

Embodiment 18

The method of Embodiment 16, wherein the antibody-drug conjugate or the means for delivering a cytotoxic agent to Her2$^+$ cells, is A166, ALT-P7, ARX788, DHES0815A, DS-8201a, RC48, SYD985, MED14276, or XMT-1522.

Embodiment 19

The method of any one of Embodiments 1-12, wherein the Her2-targeted therapeutic agent, or the small molecule means for inhibiting Her2 kinase activity, comprises a Her2 kinase inhibitor.

Embodiment 20

The method of Embodiment 19, wherein the Her2 kinase inhibitor is lapatinib or neratinib.

Embodiment 21

The method of Embodiment 19, wherein the Her2 kinase inhibitor is afatinib or dacomitinib.

Embodiment 22

The method of any one of Embodiments 1-21, wherein the treatment is applied as a debulking therapy.

Embodiment 23

The method of any one of Embodiments 1-21, wherein the treatment is applied as adjuvant therapy.

Embodiment 24

The method of any one of Embodiments 1-23, wherein the Her2$^+$ cancer is Her2$^+$ breast cancer.

Embodiment 25

The method of any one of Embodiments 1-23, wherein the Her2$^+$ cancer is Her2$^+$ gastroesophageal cancer, ovarian cancer, stomach cancer, adenocarcinoma of the lung, uterine cancer (such as serous endometrial carcinoma), or salivary duct carcinoma.

Embodiment 26

The method of any one of Embodiments 1-25, wherein a therapeutic response to the RXR agonist and the Her2-targeted therapeutic agent is greater than to the response to either of the agents alone.

Embodiment 27

The method of Embodiment 26, wherein the greater therapeutic response is a slowing of tumor growth, stabilization of disease, a partial response, a complete response, extended overall survival, or disease-free survival.

Embodiment 28

The method of Embodiment 26 or 27, wherein response is evaluated according to RECIST or iRECIST criteria.

Embodiment 29

The method of any one of Embodiments 26-28, comprising a reduction or amelioration of secondary symptoms.

Embodiment 30

A combination comprising a Her2-targeted therapeutic agent, or means for therapeutically targeting Her2, and a RXR agonist of Formula I,

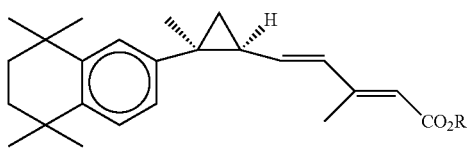
(Formula I)

wherein R is H, or lower alkyl of 1 to 6 carbons; or a pharmaceutically-acceptable salt thereof.

Embodiment 31

The combination of Embodiment 30, wherein the Her2-targeted therapeutic agent, or means for therapeutically targeting Her2, comprises:
means for inhibiting Her2$^+$ tumor cell proliferation,
means for mediating ADCC of Her2$^+$ tumor cells,
immunoglobulin means for inhibiting Her2 signaling,
means for delivering a cytotoxic agent to Her2$^+$ cells, or
small molecule means for inhibiting Her2 kinase activity.

Embodiment 32

The combination of Embodiment 30 or 31, further comprising thyroid hormone.

Embodiment 33

The combination of any one of Embodiments 30-32, wherein the RXR agonist is a compound of Formula II

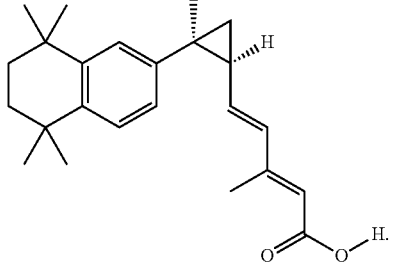
(Formula II)

Embodiment 34

The combination of any one of Embodiments 30-33, wherein:
the Her2-targeted therapeutic agent,
the means for inhibiting Her2$^+$ tumor cell proliferation,
the means for mediating ADCC of Her2$^+$ tumor cells,
the immunoglobulin means for inhibiting Her2 signaling, or
the means for delivering a cytotoxic agent to Her2$^+$ cells, comprises an anti-Her2 therapeutic antibody.

Embodiment 35

The combination of Embodiment 34, wherein the therapeutic antibody is trastuzumab or pertuzumab.

Embodiment 36

The combination of any one of Embodiments 30-34, wherein the Her2-targeted therapeutic agent, the means for inhibiting Her2$^+$ tumor cell proliferation, or the immunoglobulin means for inhibiting Her2 signaling, comprises an antibody-drug conjugate wherein the antibody is an anti-Her2 antibody.

Embodiment 37

The combination of Embodiment 36, wherein the antibody-drug conjugate is ado-trastuzumab emtansine.

Embodiment 38

The combination of any one of Embodiments 30-33, wherein the Her2-targeted therapeutic agent, or the small molecule means for inhibiting Her2 kinase activity, comprises a Her2 kinase inhibitor.

Embodiment 39

The combination of Embodiment 38, wherein the Her2 kinase inhibitor is lapatinib or neratinib.

Embodiment 40

A kit comprising the combination of any one of Embodiments 30-39.

Embodiment 41

A RXR agonist of Formula I,

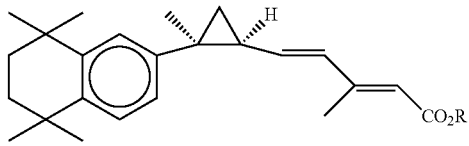
(Formula I)

wherein R is H, or lower alkyl of 1 to 6 carbons; or a pharmaceutically-acceptable salt thereof, for use in treating a patient with Her2$^+$ cancer, wherein the patient has received, is receiving, or is scheduled to receive a Her2-targeted therapeutic agent.

Embodiment 42

A RXR agonist of Formula I,

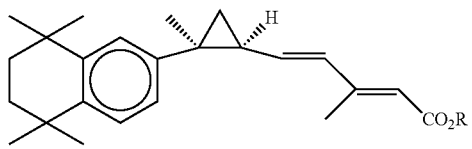

(Formula I)

wherein R is H, or lower alkyl of 1 to 6 carbons; or a pharmaceutically-acceptable salt thereof, and a Her2-targeted therapeutic agent for use in combination in treating a patient with Her2+ cancer.

Embodiment 43

A combination of a RXR agonist of Formula I,

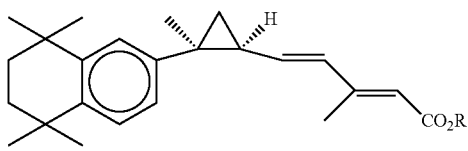

(Formula I)

wherein R is H, or lower alkyl of 1 to 6 carbons; or a pharmaceutically-acceptable salt thereof, and a Her2-targeted therapeutic agent for use in treating a patient with Her2+ cancer.

Embodiment 44

A pharmaceutical combination for treating Her2+ cancer comprising a RXR agonist of Formula I,

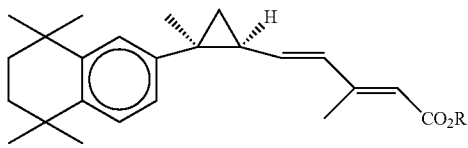

(Formula I)

wherein R is H, or lower alkyl of 1 to 6 carbons; or a pharmaceutically-acceptable salt thereof, and a Her2-targeted therapeutic agent.

Embodiment 45

A RXR agonist of Formula I,

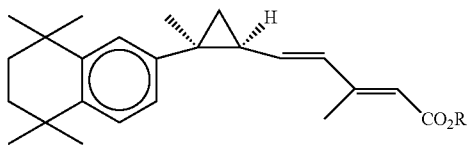

(Formula I)

wherein R is H, or lower alkyl of 1 to 6 carbons; or a pharmaceutically-acceptable salt thereof, for use in manufacturing a medicament for treating Her2+ cancer, in a patient who has received, is receiving, or is scheduled to receive a Her2-targeted therapeutic agent.

Embodiment 46

A RXR agonist of Formula I,

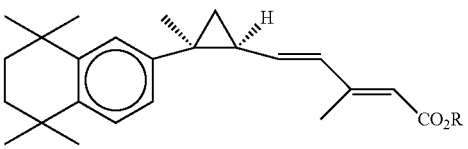

(Formula I)

wherein R is H, or lower alkyl of 1 to 6 carbons; or a pharmaceutically-acceptable salt thereof, and a Her2-targeted therapeutic agent, for use in manufacturing medicaments for use together to treat Her2+ cancer.

Embodiment 47

A Her2-targeted therapeutic agent for treating Her2+ cancer in a patient with Her2+ cancer, with a therapeutic response less than a complete response to treatment with a RXR agonist of Formula I,

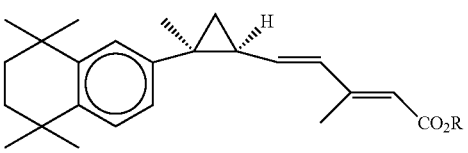

(Formula I)

wherein R is H, or lower alkyl of 1 to 6 carbons; or a pharmaceutically-acceptable salt thereof,
in combination with the RXR agonist.

Embodiment 48

A RXR agonist of Formula I,

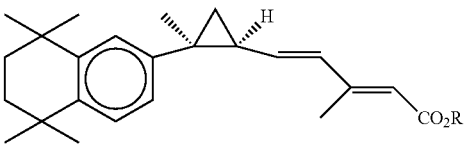

(Formula I)

wherein R is H, or lower alkyl of 1 to 6 carbons; or a pharmaceutically-acceptable salt thereof, for treating Her2+ cancer in a patient with Her2+ cancer, with a therapeutic response less than a complete response to treatment with a Her2-targeted therapeutic agent, in combination with the Her2-targeted therapeutic agent.

It should be manifest that each or Embodiments 41-48 can be modified in a manner similar to the modification of Embodiments 1-5 and 7 by Embodiments 5 and 8-29.

EXAMPLES

The following non-limiting examples are provided for illustrative purposes only in order to facilitate a more complete understanding of representative embodiments now contemplated. These examples should not be construed to limit any of the embodiments described in the present specification,

Example 1

Inhibition of Breast Cancer Cell Growth by IRX4204 Plus Trastuzumab

Figure 1B:
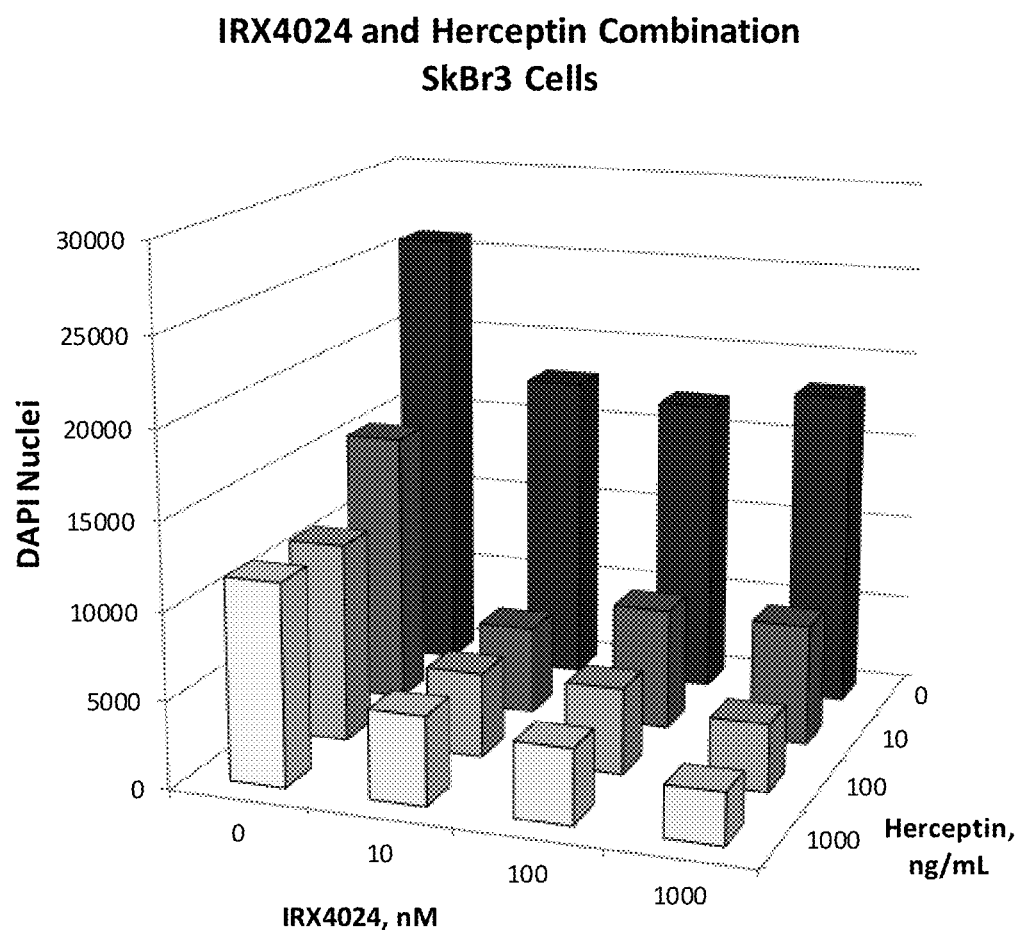
Figure 2A:
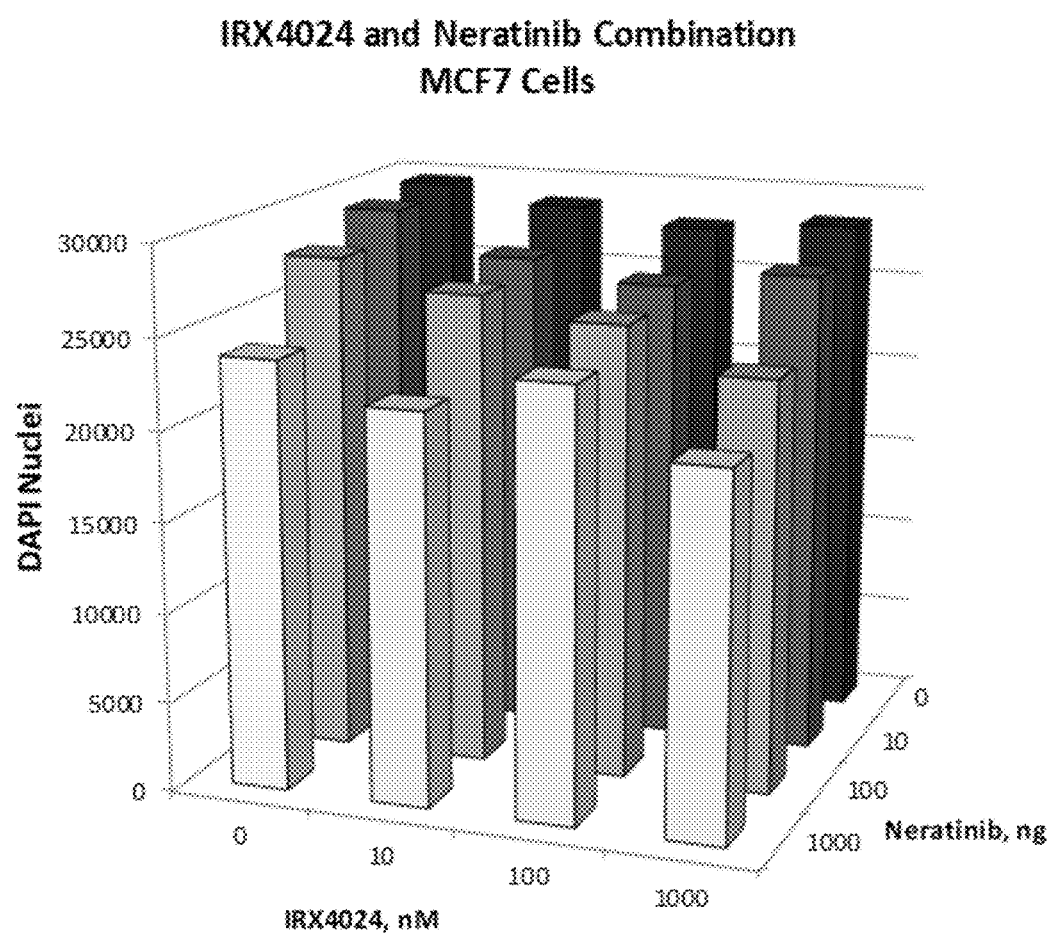
FIGS. 2A-D are three-dimensional plots depicting the growth inhibitory effects of IRX4204 and lapatinib, alone and in combination, on breast cancer cell lines: MCF7 cells (FIG. 2A), SkBr3 cells (FIG. 2B), BT474 cells (FIG. 2C), and MDA-MB-361 cells (FIG. 2D).
Figure 2B:
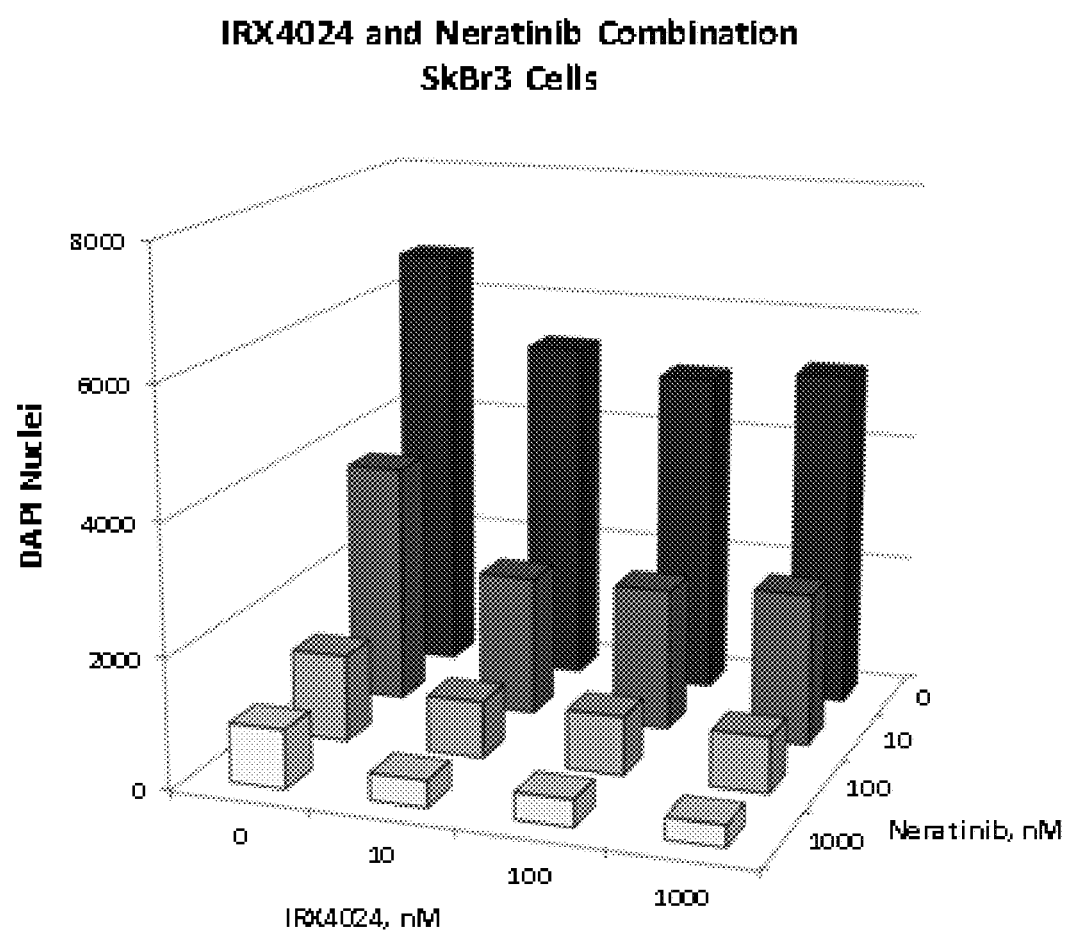
Figure 2C:
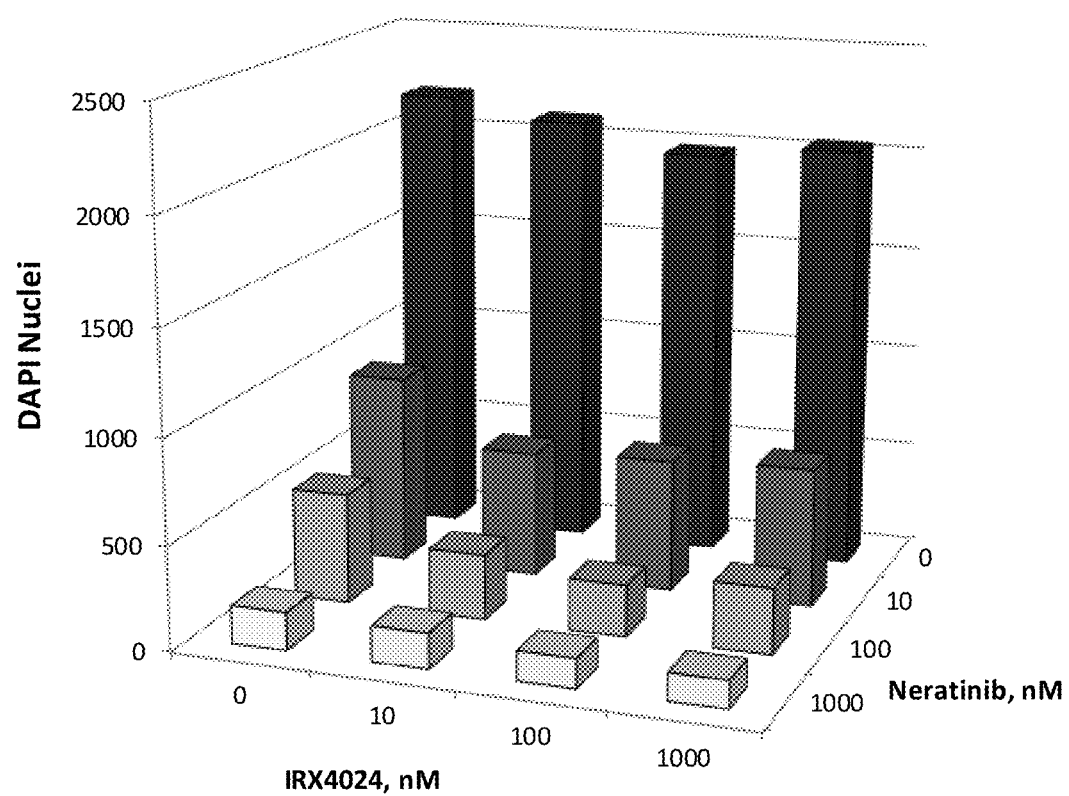
Figure 2D:
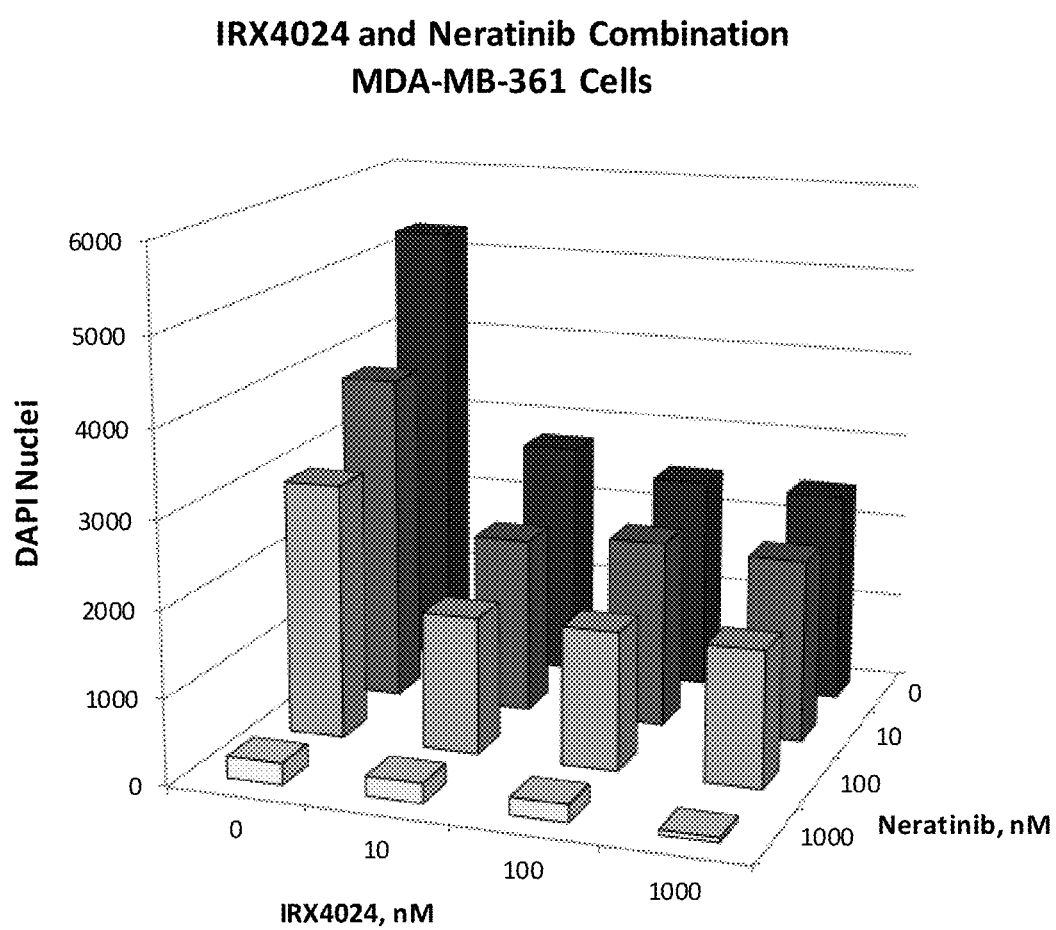
Figure 3A:
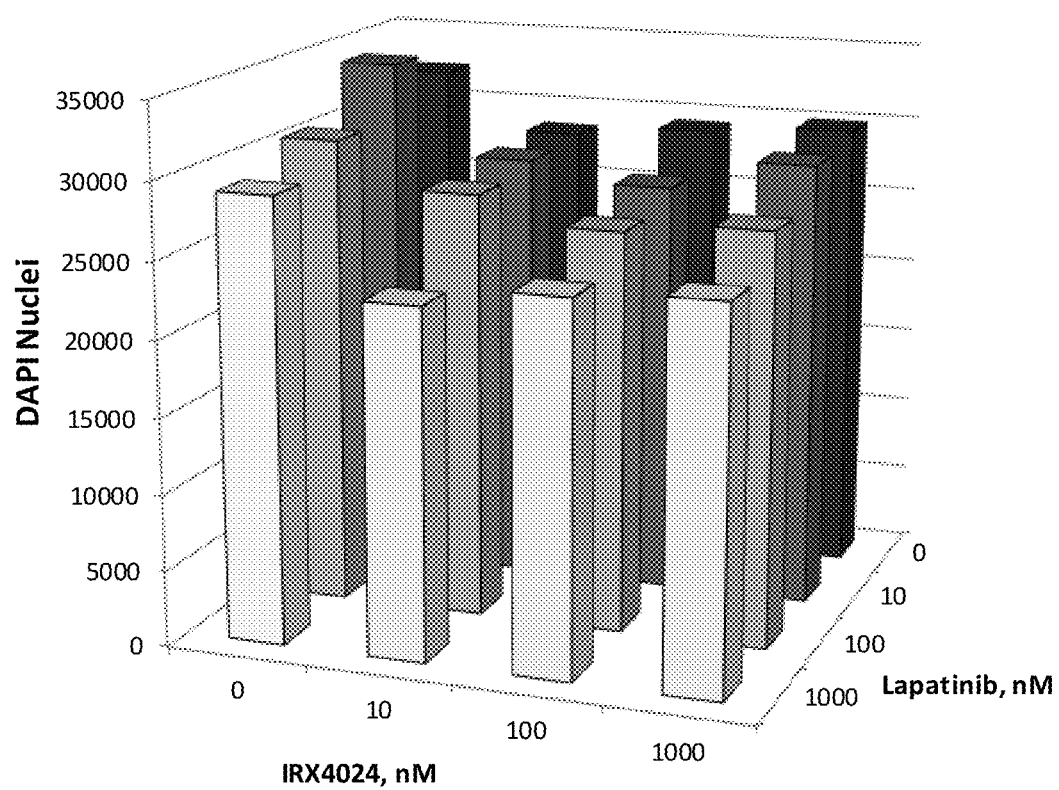
FIGS. 3A-D are three-dimensional plots depicting the growth inhibitory effect of IRX4204 and neratinib, alone and in combination, on breast cancer cell lines: MCF7 cells (FIG. 3A), SkBr3 cells (FIG. 3B), BT474 cells (FIG. 3C), and MDA-MB-361 cells (FIG. 3D).
Figure 3B:
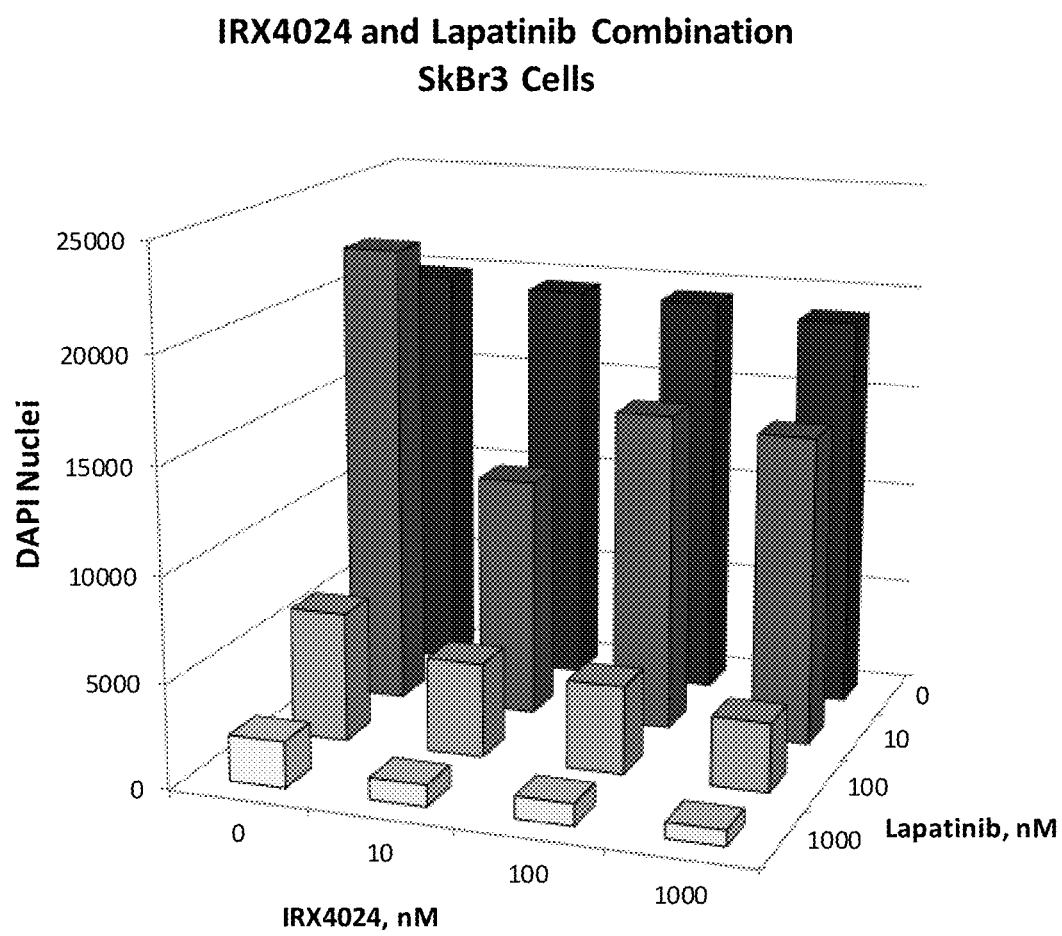
Figure 3C:
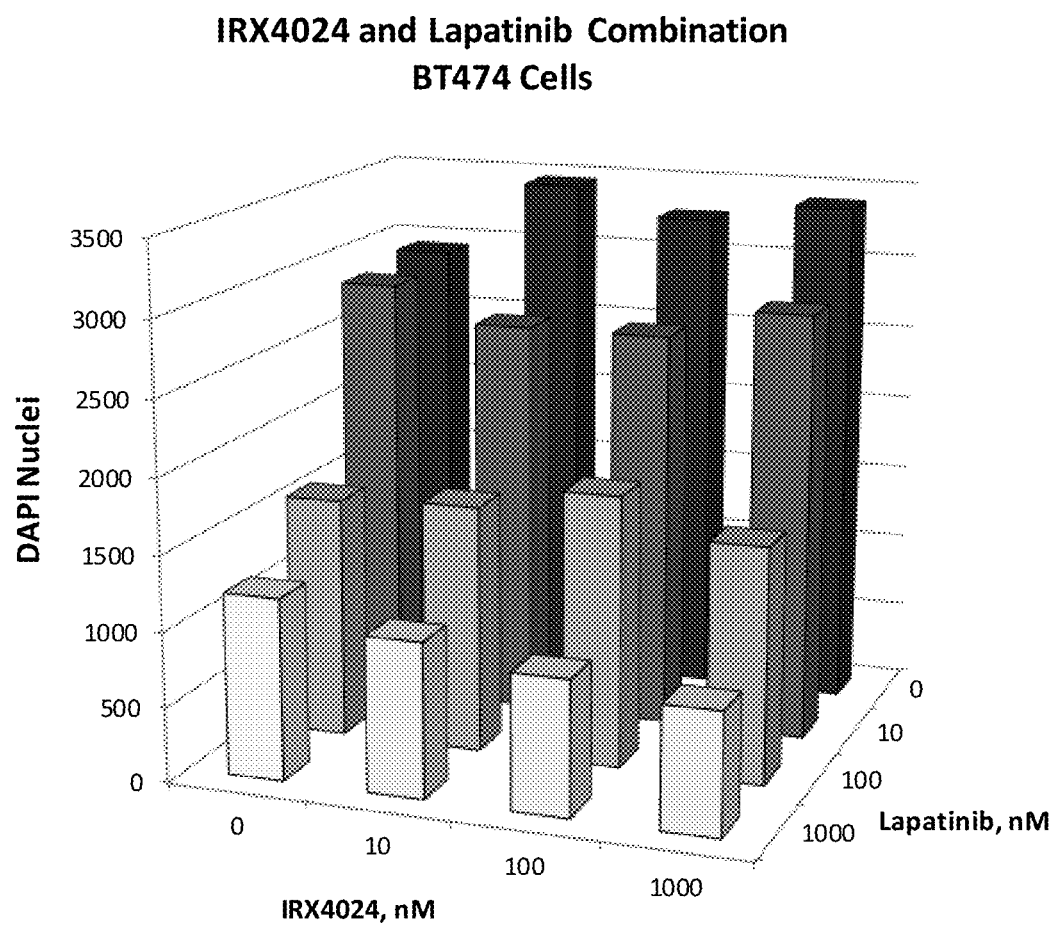
Figure 3D:
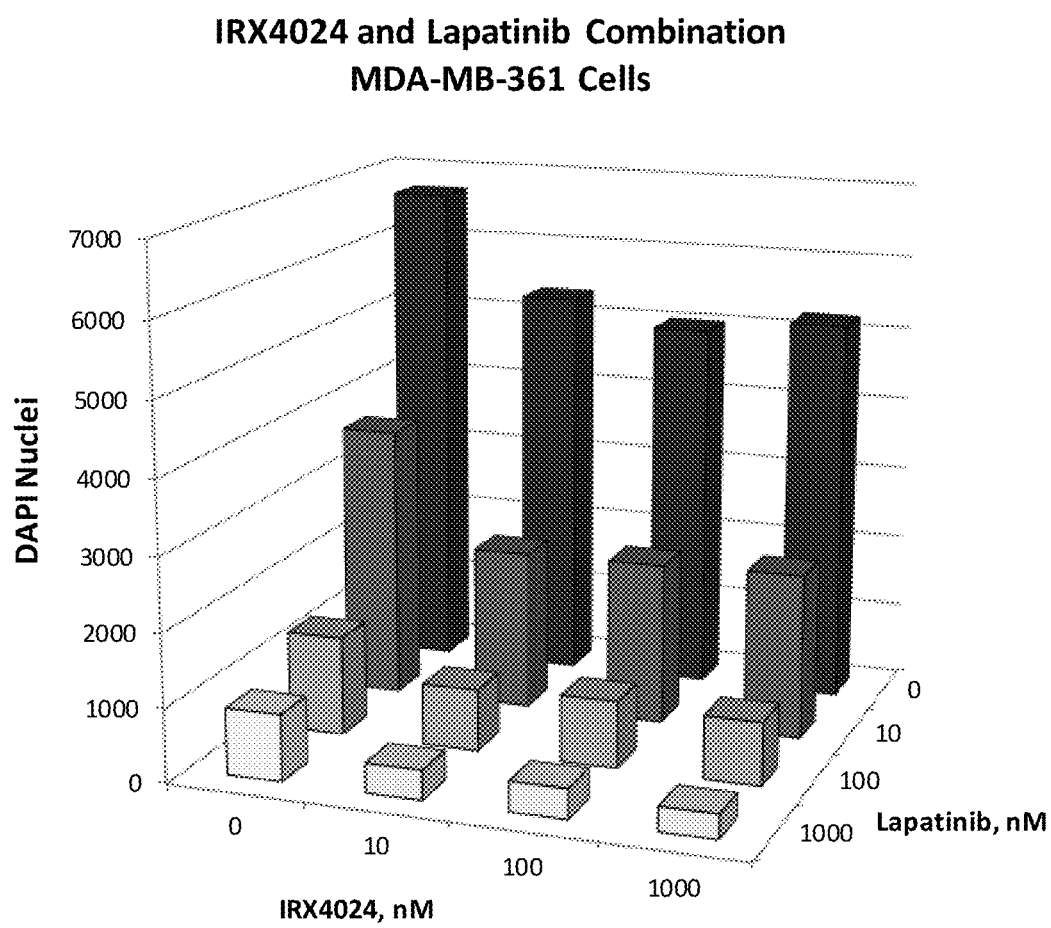

Two breast cancer cell lines, MCF7 and SkBr3 were cultured in the presence of 0, 10, 100, or 1000 nM IRX4204 and 0, 0.1, 1, or 10 µg/ml trastuzumab. MCF7 is an $ER^+PR^+$ $Her2^-$ cell line. SkBr3 is an $ER^-$ $PR^-$ $Her2^+$ cell line. Cells were plated in 96 well optical plates and IRX-4204 and trastuzumab were added 24 hours after cell plating. After a further 6 days, the cells were fixed with 4% paraformaldehyde in phosphate buffered saline (PBS). Nuclei were then stained with DAPI and imaged with the MetaXpress® microscope (Molecular Devices, San Jose, Calif.). Cell nuclei were segmented then counted by defining pixel intensity over background and object size, using the algorithm of the MetaXpress® image analysis software. Experimental data points were performed at a minimum of quadruplicate, and results were reported as average cell count±standard deviation (SD). As seen in FIG. 1A, neither agent had more than marginal effect on the $Her2^-$MCF7 cell line. As seen in FIG. 1B, both agents individually have a moderate growth inhibitory effect on the $Her2^+$ SkBr3 cell line, and had a very substantial, growth inhibitory effect when used in combination, even at the lowest concentrations tested.

To assess if this improved growth inhibition effect was synergistic, the percent inhibition observed for the highest concentrations of the combined therapeutic agents was compared to the percent inhibition that would be expected for the combination based on the observed inhibition of the therapeutic agents used alone, if the agents acting independently, that is, without interaction (see Table 1). That is, PAE= (FE1+((1−FE1)×FE2))×100, where PAE is the predicted additive effect, FE1 is the observed fractional effect of a 1st treatment, and FE2 is the observed fractional effect of a 2nd treatment.

TABLE 1

Synergistic Effect of the Combination of IRX4204 and Trastuzumab on the Inhibition of the Growth of SkBr3 Cells.

| Treatment | DAPI Nuclei Count | % Inhibition | |
|---|---|---|---|
| Control | 25958 | | |
| IRX4204 1000 nM | 18274 | 29.4 | If Additive = |
| Herceptin 1000 ng | 11582 | 55.4 | 68.5% |
| IRX4204 + Herceptin | 2946 | 88.7 | |

Whereas the combined inhibitory effect of IRX4204 and trastuzumab would be predicted to be 68.5% if there was no interaction between the effects of the two agents, in fact the observed degree of inhibition was 88.7%, clearly indicating that IRX4204 and trastuzumab interact in a synergistic manner.

Example 2

Inhibition of Breast Cancer Cell Growth by IRX4204 Plus Lapatinib or Neratinib

The experiment of Example 1 was repeated using the Her2 kinase inhibitors lapatinib or neratinib instead of trastuzumab at 0, 0.1, 1, or 10 nM. Additionally the panel of breast cancer cell lines was expanded to also include the $ER^+PR^+Her2^+$ cell line BT474 and the $ER^+PR^-$ $Her2^+$ cell line MDA-MB-361. The general pattern seen above, that the $Her2^-$MCF7 cell line showed generally marginal response to the treatments and that the $Her^+$ cell lines exhibited a greater degree of inhibition to the combination than either agent alone, was again observed (see FIGS. 2 and 3).

To assess if this improved growth inhibition effect was synergistic, the percent inhibition observed for the highest concentrations of the combined therapeutic agents was compared to the percent inhibition that would be expected for the combination based on the observed inhibition of the therapeutic agents used alone, if the agents acting independently, that is, without interaction (see Tables 2-4).

TABLE 2

Synergistic Effect of the Combination of IRX4204 and Lapatinib or Neratinib on the Inhibition of the Growth of SkBr3 Cells.

| Treatment | DAPI Nuclei Count | % Inhibition | |
|---|---|---|---|
| Control | 19855 | | |
| IRX4204 1000 nM | 18906 | 4.8 | If Additive = |
| Lapatinib 1000 nM | 2211 | 88.9 | 89.4% |
| IRX4204 + Lapatinib | 743 | 96.3 | |
| Control | 6696 | | |
| IRX4204 1000 nM | 5218 | 22.1 | If Additive = |
| Neratinib 1000 nM | 903 | 86.5 | 89.5% |
| IRX4204 + Neratinib | 329 | 95.1 | |

TABLE 3

Synergistic Effect of the Combination of IRX4204 and Lapatinib or Neratinib on the Inhibition of the Growth of BT474 Cells.

| Treatment | DAPI Nuclei Count | % Inhibition | |
|---|---|---|---|
| Control | 2937 | | |
| IRX4204 1000 nM | 3399 | −15.7* | If Additive = |
| Lapatinib 1000 nM | 1211 | 58.8 | 58.8% |
| IRX4204 + Lapatinib | 813 | 72.3 | |
| Control | 2192 | | |
| IRX4204 1000 nM | 2043 | 6.8 | If Additive = |
| Neratinib 1000 nM | 180 | 91.8 | 92.4% |
| IRX4204 + Neratinib | 130 | 94.1 | |

*Zero inhibition used in calculation of predicted additive effect

TABLE 4

Synergistic Effect of the Combination of IRX4204 and Lapatinib or Neratinib on the Inhibition of the Growth of MDA-MB-361 Cells.

| Treatment | DAPI Nuclei Count | % Inhibition | |
|---|---|---|---|
| Control | 6696 | | |
| IRX4204 1000 nM | 5218 | 22.1 | If Additive = |
| Lapatinib 1000 nM | 903 | 86.5 | 89.5% |
| IRX4204 + Lapatinib | 329 | 95.2 | |
| Control | 5297 | | |
| IRX4204 1000 nM | 2459 | 43.6 | If Additive = |
| Neratinib 1000 nM | 249 | 95.3 | 97.3% |
| IRX4204 + Neratinib | 57 | 98.9 | |

In each case the observed degree of inhibition exceeded that predicted if there was no interaction between the effects of the two agents, even though in some cases the individual therapeutic agents were quite effective alone, leaving little room for synergy to be observed. These data also clearly indicate that IRX4204 and the small molecule Her2 kinase inhibitors interact in a synergistic manner.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A method of treating a patient with Her2+breast cancer comprising administering a RXR agonist of Formula I,

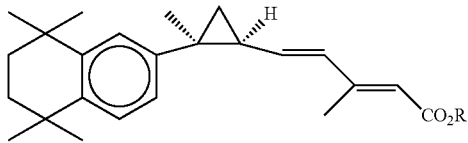

(Formula I)

wherein R is H, or lower alkyl of 1 to 6 carbons; or a pharmaceutically-acceptable salt thereof, to the patient, wherein the patient is receiving, or is scheduled to receive a Her2-targeted therapeutic antibody.

2. The method of claim 1, comprising administering a Her2-targeted therapeutic antibody.

3. A method of treating a patient with Her2+breast cancer undergoing treatment with a Her2-targeted therapeutic antibody, wherein there is evidence of therapeutic effect that is less than a complete response, comprising continuing treatment with the Her2-targeted therapeutic antibody and initiating treatment with a RXR agonist of Formula I,

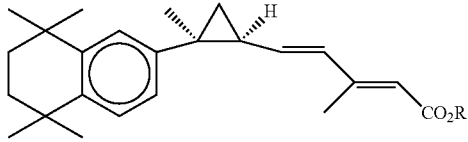

(Formula I)

wherein R is H, or lower alkyl of 1 to 6 carbons; or a pharmaceutically-acceptable salt thereof.

4. The method of claim 1, further comprising administering thyroid hormone in conjunction with the RXR agonist.

5. The method of claim 1, wherein the RXR agonist is a compound of Formula I.

6. The method of claim 1, wherein the RXR agonist is a compound of Formula II

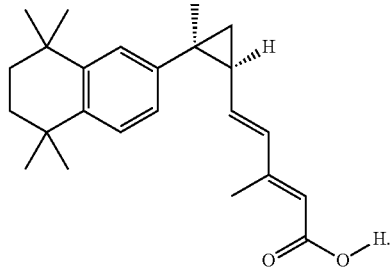

(Formula II)

7. The method of claim 1, wherein the therapeutic antibody is trastuzumab.

8. The method of claim 1, wherein the therapeutic antibody is pertuzumab.

9. The method of claim 1, wherein the patient is receiving, or is scheduled to receive a single Her2-targeted therapeutic antibody.

10. The method of claim 3, wherein the patient is undergoing treatment with a single Her2-targeted therapeutic antibody.

11. The method of claim 3, further comprising administering thyroid hormone in conjunction with the RXR agonist.

12. The method of claim 3, wherein the RXR agonist is a compound of Formula I.

13. The method of claim 3, wherein the RXR agonist is a compound of Formula II

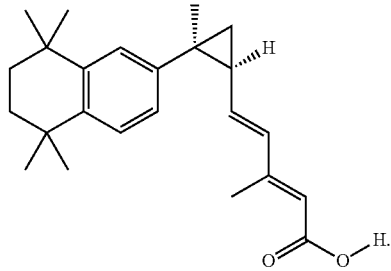

(Formula II)

14. The method of claim 3, wherein the therapeutic antibody is trastuzumab.

15. The method of claim 3, wherein the therapeutic antibody is pertuzumab.

16. The method of claim 1, wherein the inhibition of tumor cell growth by the combination of the Her2-targeted therapeutic antibody and the RXR agonist is greater than additive effects of each of the Her2-targeted therapeutic antibody and the RXR agonist alone.

17. The method of claim 3, wherein the inhibition of tumor cell growth by the combination of the Her2-targeted therapeutic antibody and the RXR agonist is greater than additive effects of each of the Her2-targeted therapeutic antibody and the RXR agonist alone.

* * * * *